(12) United States Patent
Shingel et al.

(10) Patent No.: US 8,871,713 B2
(45) Date of Patent: Oct. 28, 2014

(54) FORMULATIONS OF GROWTH HORMONE RELEASING FACTOR (GRF) MOLECULES WITH IMPROVED STABILITY

(71) Applicant: Theratechnologies Inc., Montreal (CA)

(72) Inventors: Kirill I Shingel, Brossard (CA); Daniel Fleury, Saint-Hubert (CA)

(73) Assignee: Theratechnologies Inc., Montreal, Quebec (CA)

( * ) Notice: Subject to any disclaimer, the term of this patent is extended or adjusted under 35 U.S.C. 154(b) by 0 days.

(21) Appl. No.: 13/803,712

(22) Filed: Mar. 14, 2013

(65) Prior Publication Data
US 2014/0249083 A1    Sep. 4, 2014

Related U.S. Application Data

(60) Provisional application No. 61/771,244, filed on Mar. 1, 2013.

(51) Int. Cl.
*A61K 38/26* (2006.01)
*A61K 47/40* (2006.01)
*A61K 47/48* (2006.01)

(52) U.S. Cl.
CPC ........... *A61K 47/48023* (2013.01); *A61K 47/40* (2013.01); *A61K 38/26* (2013.01)
USPC ........................................ 514/11.7; 514/777

(58) Field of Classification Search
CPC ... C07K 14/605; A61K 38/26; A61K 49/189; A61K 51/1268
See application file for complete search history.

(56) References Cited

U.S. PATENT DOCUMENTS

| | | | |
|---|---|---|---|
| 5,861,379 A | 1/1999 | Ibea et al. | |
| 5,939,386 A | 8/1999 | Ibea et al. | |
| 6,020,311 A * | 2/2000 | Brazeau et al. | 514/4.8 |
| 6,429,195 B1 | 8/2002 | Foster et al. | |
| 2005/0197288 A1 | 9/2005 | Abribat et al. | |
| 2007/0219124 A1* | 9/2007 | Labischinski et al. | 514/8 |
| 2008/0038292 A1* | 2/2008 | Arvinte et al. | 424/198.1 |
| 2008/0249017 A1* | 10/2008 | Loughrey et al. | 514/12 |
| 2012/0232001 A1 | 9/2012 | Prestrelski et al. | |

FOREIGN PATENT DOCUMENTS

| | | |
|---|---|---|
| CA | 1328634 C | 4/1994 |
| WO | 2005037307 A1 | 4/2005 |

OTHER PUBLICATIONS

Rasheed et al. ("Cyclodextrins as Drug Carrier Molecule: A Review," Sci. Pharm. 2008; 76: 567-598).*
Aachmann F.L., Structural Background of Cyclodextrin-Protein Interactions, Protein Engineering, 2003, 16:905-912.
Balestrieri et al., Second-derivative spectroscopy of proteins. A method for the quantitative determination of aromatic amino acids in proteins. Eur. J. Biochem. , 1978, 90:433-440.
Baudyš M. and Kim S.W., Peptide and Protein Characterization, Chapter 4, pp. 41-69, in Frokjaer S., Hovgaard L. (Eds.) Pharmaceutical formulation Development of Peptides and Proteins. Taylor & Francis, 2000.
Bongers et al., Degradation of aspartic acid and asparagines residues in human growth hormone-relasing factor. Int. J. Peptide Protein Res., 1992, 39:364-374.
Brewster et al., Use of 2-Hydroxypropyl-β-cyclodextrin as a Solubilizing and Stabilizing Excipient for Protein Drugs. Pharm. Res.,1991, 8:792-795.
Fang et al., Effects of Excipients on the Chemical and Physical Stability of Glucagon during Freeze-Drying and Storage in Dried Formulations, Pharm Res., 2012, 29:3278-3291.
Fry et al., Solution structures of cyclic and dicyclic analogues of growth hormone releasing factor as determined by two-dimensional NMR and CD spectroscopies and constrained molecular dynamics. Biopolymers, 1992, 32:649-666.
Hekman et al., Isolation and identification of cyclic imide and deamidation products in heat stressed pramlintide injection drug product. J. Pharm. Biomed Anal., 1999, 20:763-77.
Johnson et al., Solubilization of a tripeptide HIV protease inhibitor using a combination of ionization and complexation with chemically modified cyclodextrins. J. Pharm. Sci. , 1994, 83:1142-11.
Kamerzell T.J. and Middaugh R., The complex inter-relationships between protein flexibility and stability. J. Pharm. Sci., 2008, 97:3494-3517.
Kosky et al., The effects of alpha-helix on the stability of Asn residues: Deamidation rates in peptides of varying helicity, Protein Science, 1999, 8:2519-2523.
Loftsson et al., Pharmaceuticals application of cyclodextrins, Journal of Pharmaceutical Sciences, 1996, 85:1017-1025.
Manning et al., Stability of Protein Pharmaceuticals: An Update, Pharmaceutical Research, 2010, 27:544-575.
Markell et al., Pharmaceutical significance of the cyclic imide forms of recombinant human glial cell derived neutrophic factor. Pharm Res. , 2001,18:1361-1366.
Miclo et al., Determination of the aromatic amino acids residue by first- and second-derivative UV spectrometry for a simple characterization of peptides. Int. J. Peptide Protein Res., 1995, 46:186-192.
Mrozek et al., Influence of the separation of the charged groups and aromatic ring on interactions of tyrosine and phenylalanine analogues and derivatives with β-cyclodextrin. Biophys. Chem., 2005, 116:237-250.

(Continued)

*Primary Examiner* — Christina Bradley
(74) *Attorney, Agent, or Firm* — Fish & Richardson P.C.

(57) ABSTRACT

Stabilized solid and liquid pharmaceutical formulations comprising a GRF molecule as active ingredient, such as GRF analogs including those comprising an N-terminal-attached hydrophobic moiety, such as [trans-3-hexenoyl]hGHRH (1-44) amide, are disclosed. The formulation comprises a GRF molecule or a pharmaceutically acceptable salt thereof and a β-cyclodextrin which is not conjugated to the GRF molecule or salt thereof. Also disclosed is the use of the formulation for the treatment of various conditions, methods of preparing the formulation, as well as kits containing it. Methods of stabilizing (e.g., with respect to chemical stability) such GRF molecules, as well as methods of inhibiting their deamidation at $Asn^8$, are also disclosed.

23 Claims, 16 Drawing Sheets

(56) References Cited

OTHER PUBLICATIONS

Robinson N. E. and Robinson A.B., Prediction of protein deamidation rates from primary and three-dimensional structure. Proc. Natl. Acad. Sci. USA, 2001, 98:4367-4372.

Shahrokh et al., Major degradation products of basic fibroblast growth factor: detection of succinimide and iso-aspartate in place of aspartate. Pharm. Res., 1994, 11:936-944.

Stevenson et al., Effect of secondary structure on the rate of deamidation of several growth hormone releasing analogues. Int. J. peptide Res., 1993, 42:497-503.

Violand et al., Isolation and characterization of porcine somatotropin containing a succinimide residue in place of aspartate129. Prot. Sci., 1992, 1:1634-1641.

Zhang et al., Effects of Hydroxylpropyl-B-Cyclodextrin on in Vitro Insulin Stability, Int. J. Mol. Sci., 2009, 10:2031-2040.

Zhang et al., A New Strategy for Enhancing the Stability of Lyophilized Protein: The Effect of the Reconstitution Medium on Keratinocyte Growth Factor. Pharm. Res., 1995, 12:1447-1452.

International Search Report and Written Opinion dated May 9, 2014 for International Application No. PCT/CA2014/050134.

* cited by examiner

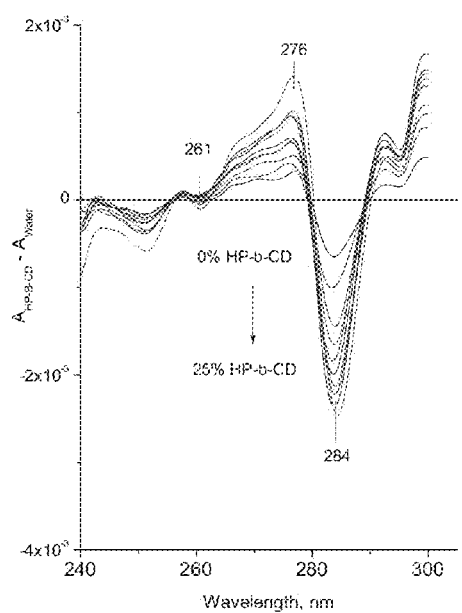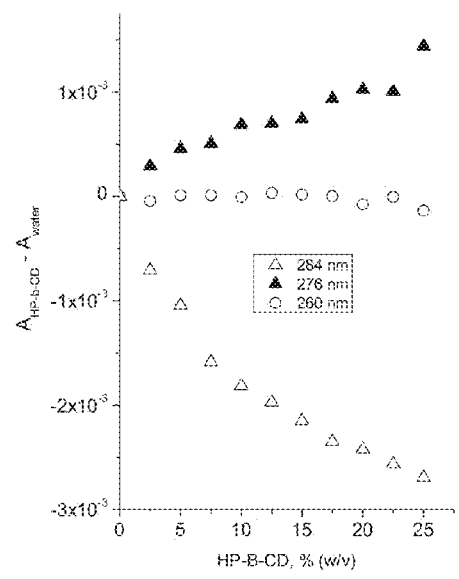
FIGURE 10
FIGURE 11

SEQUENCE LISTING

```
<160> NUMBER OF SEQ ID NOS: 7

<210> SEQ ID NO 1
<211> LENGTH: 44
<212> TYPE: PRT
<213> ORGANISM: Artificial sequence
<220> FEATURE:
<223> OTHER INFORMATION: GRF peptide
<220> FEATURE:
<221> NAME/KEY: VARIANT
<222> LOCATION: (1)..(1)
<223> OTHER INFORMATION: Xaa = Tyr or His
<220> FEATURE:
<221> NAME/KEY: VARIANT
<222> LOCATION: (2)..(2)
<223> OTHER INFORMATION: Xaa = Val or Ala
<220> FEATURE:
<221> NAME/KEY: VARIANT
<222> LOCATION: (13)..(13)
<223> OTHER INFORMATION: Xaa = Val or Ile
<220> FEATURE:
<221> NAME/KEY: VARIANT
<222> LOCATION: (15)..(15)
<223> OTHER INFORMATION: Xaa = Ala or Gly
<220> FEATURE:
<221> NAME/KEY: VARIANT
<222> LOCATION: (18)..(18)
<223> OTHER INFORMATION: Xaa = Ser or Tyr
<220> FEATURE:
<221> NAME/KEY: VARIANT
<222> LOCATION: (24)..(24)
<223> OTHER INFORMATION: Xaa = Gln or His
<220> FEATURE:
<221> NAME/KEY: VARIANT
<222> LOCATION: (25)..(25)
<223> OTHER INFORMATION: Xaa = Asp or Glu
<220> FEATURE:
<221> NAME/KEY: VARIANT
<222> LOCATION: (27)..(27)
<223> OTHER INFORMATION: Xaa = Met or Ile or Nle
<220> FEATURE:
<221> NAME/KEY: VARIANT
<222> LOCATION: (28)..(28)
<223> OTHER INFORMATION: Xaa = Ser or Asn
<220> FEATURE:
<221> NAME/KEY: VARIANT
<222> LOCATION: (30)..(30)
<223> OTHER INFORMATION: Xaa = any amino acid or is absent
<220> FEATURE:
<221> NAME/KEY: VARIANT
<222> LOCATION: (31)..(31)
<223> OTHER INFORMATION: Xaa = any amino acid or is absent
```

```
<220> FEATURE:
<221> NAME/KEY: VARIANT
<222> LOCATION: (32)..(32)
<223> OTHER INFORMATION: Xaa = any amino acid or is absent
<220> FEATURE:
<221> NAME/KEY: VARIANT
<222> LOCATION: (33)..(33)
<223> OTHER INFORMATION: Xaa = any amino acid or is absent
<220> FEATURE:
<221> NAME/KEY: VARIANT
<222> LOCATION: (34)..(34)
<223> OTHER INFORMATION: Xaa = any amino acid or is absent
<220> FEATURE:
<221> NAME/KEY: VARIANT
<222> LOCATION: (35)..(35)
<223> OTHER INFORMATION: Xaa = any amino acid or is absent
<220> FEATURE:
<221> NAME/KEY: VARIANT
<222> LOCATION: (36)..(36)
<223> OTHER INFORMATION: Xaa = any amino acid or is absent
<220> FEATURE:
<221> NAME/KEY: VARIANT
<222> LOCATION: (37)..(37)
<223> OTHER INFORMATION: Xaa = any amino acid or is absent
<220> FEATURE:
<221> NAME/KEY: VARIANT
<222> LOCATION: (38)..(38)
<223> OTHER INFORMATION: Xaa = any amino acid or is absent
<220> FEATURE:
<221> NAME/KEY: VARIANT
<222> LOCATION: (39)..(39)
<223> OTHER INFORMATION: Xaa = any amino acid or is absent
<220> FEATURE:
<221> NAME/KEY: VARIANT
<222> LOCATION: (40)..(40)
<223> OTHER INFORMATION: Xaa = any amino acid or is absent
<220> FEATURE:
<221> NAME/KEY: VARIANT
<222> LOCATION: (41)..(41)
<223> OTHER INFORMATION: Xaa = any amino acid or is absent
<220> FEATURE:
<221> NAME/KEY: VARIANT
<222> LOCATION: (42)..(42)
<223> OTHER INFORMATION: Xaa = any amino acid or is absent
<220> FEATURE:
<221> NAME/KEY: VARIANT
<222> LOCATION: (43)..(43)
<223> OTHER INFORMATION: Xaa = any amino acid or is absent
<220> FEATURE:
<221> NAME/KEY: VARIANT
<222> LOCATION: (44)..(44)
<223> OTHER INFORMATION: Xaa = any amino acid or is absent

<400> SEQUENCE: 1

Xaa Xaa Asp Ala Ile Phe Thr Asn Ser Tyr Arg Lys Xaa Leu Xaa Gln
1               5                   10                  15

Leu Xaa Ala Arg Lys Leu Leu Xaa Xaa Ile Xaa Xaa Arg Xaa Xaa Xaa
                20                  25                  30

Xaa Xaa Xaa Xaa Xaa Xaa Xaa Xaa Xaa Xaa Xaa Xaa
            35                  40

<210> SEQ ID NO 2
<211> LENGTH: 44
<212> TYPE: PRT
<213> ORGANISM: Homo sapiens
<220> FEATURE:
<221> NAME/KEY: MISC_FEATURE
<222> LOCATION: (44)..(44)
<223> OTHER INFORMATION: Leu residue is capped with an unsubstituted
      amide moiety

<400> SEQUENCE: 2

Tyr Ala Asp Ala Ile Phe Thr Asn Ser Tyr Arg Lys Val Leu Gly Gln
1               5                   10                  15
```

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 3
<211> LENGTH: 44
<212> TYPE: PRT
<213> ORGANISM: Artificial sequence
<220> FEATURE:
<223> OTHER INFORMATION: Amino acid sequence of human GRF

<400> SEQUENCE: 3

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 4
<211> LENGTH: 29
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Arg residue is capped with an unsubstituted
      amide moiety

<400> SEQUENCE: 4

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 5
<211> LENGTH: 29
<212> TYPE: PRT
<213> ORGANISM: Artificial sequence
<220> FEATURE:
<223> OTHER INFORMATION: Amino acid sequence of minimum active core of
      human GRF

<400> SEQUENCE: 5

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 6
<211> LENGTH: 15
<212> TYPE: PRT
<213> ORGANISM: Artificial sequence
<220> FEATURE:
<223> OTHER INFORMATION: Amino acid sequence corresponding to positions
      30 to 44 of human GRF

<400> SEQUENCE: 6

Gln Gln Gly Glu Ser Asn Gln Glu Arg Gly Ala Arg Ala Arg Leu
1               5                   10                  15

<210> SEQ ID NO 7
<211> LENGTH: 44

```
<212> TYPE: PRT
<213> ORGANISM: Artificial sequence
<220> FEATURE:
<223> OTHER INFORMATION: Modified GRF peptide
<220> FEATURE:
<221> NAME/KEY: MISC_FEATURE
<222> LOCATION: (1)..(1)
<223> OTHER INFORMATION: Tyr residue is linked to a trans-3-hexenoyl
      moiety
<220> FEATURE:
<221> NAME/KEY: MISC_FEATURE
<222> LOCATION: (44)..(44)
<223> OTHER INFORMATION: Leu residue is capped with an unsubstituted
      amide moiety

<400> SEQUENCE: 7

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
            35                  40
```

FORMULATIONS OF GROWTH HORMONE RELEASING FACTOR (GRF) MOLECULES WITH IMPROVED STABILITY

CROSS-REFERENCE TO RELATED APPLICATIONS

The present application claims the benefit of U.S. Provisional Application No. 61/771,244 filed on Mar. 1, 2013, which is incorporated herein by reference in its entirety.

SEQUENCE LISTING

Pursuant to 37 C.F.R. 1.821(c), a sequence listing is submitted herewith as an ASCII compliant text file named "Sequence_listing.txt", created on Mar. 14, 2013 and having a size of 5551 bytes. The content of the aforementioned file is hereby incorporated by reference in its entirety.

FIELD OF THE INVENTION

The present invention relates to pharmaceutical formulations of GRF molecules, as well as methods of preparing such pharmaceutical formulations and uses thereof. Additionally, the present invention relates to methods for stabilizing a GRF molecule.

BACKGROUND OF THE INVENTION

Growth hormone (GH) or somatotropin is secreted by the pituitary gland. Its activity is fundamental for the linear growth of a young organism but also for the maintenance of the integrity at its adult state. GH acts directly or indirectly on the peripheral organs by stimulating the synthesis of growth factors (insulin-like growth factor-I or IGF-I) or of their receptors (epidermal growth factor or EGF). The direct action of GH is of the type referred to as anti-insulinic, which favors the lipolysis at the level of adipose tissues. Through its action on IGF-I (somatomedin C) synthesis and secretion, GH stimulates the growth of cartilage and the bones (structural growth), protein synthesis and cellular proliferation in multiple peripheral organs, including muscles and skin. In adults, GH participates in the maintenance of a protein anabolism state and plays a primary role in the tissue regeneration phenomenon after a trauma.

The secretion of GH by the pituitary gland is principally controlled by two hypothalamic peptides, somatostatin and growth hormone releasing factor (GRF; also known as GH-releasing hormone or GHRH). Somatostatin inhibits its secretion, whereas GRF stimulates it. Human GRF is a 44 amino acid peptide. A peptide consisting of the first 29 amino acids of human GRF (hGRF$_{(1-29)}$; sermorelin) retains the biological activity of the full-length peptide (Lance, V. A. et al., *Biochemical and Biophysical Research Communications* 1984, 119: 265-272) and has been used clinically for the treatment of GH deficiency in children (Thorner, M. et al., *Journal of Clinical Endocrinology and Metabolism* 1996, 81: 1189-1196). More recently, the potential of GRF to reverse the age-related decline in the function of the somatotrophic GH-insulin-like growth factor (IGF)-I axis has been evaluated (Khorram, O. et al., *Clinical Obstetrics and Gynecology* 2001, 44: 893-901).

Among all known GRF molecules, GRF analogs containing a hydrophobic tail as defined in the present application are modified versions or analogs of human GRF that have been shown to have higher proteolytic stability in biological milieu and as a result, these analogs were shown to display longer duration of action resulting in enhanced growth hormone secretion and insulin like growth factor-1 synthesis (U.S. Pat. Nos. 5,861,379 and 5,939,386). Due to their superior plasma stability and pharmacological properties compared to the native GRF (1-44) amide, these GRF analogs were shown to confer therapeutic efficacy in several medical conditions, e.g., wasting associated with cystic fibrosis and COPD (International Application No. WO 05/037307), recovery after hip fracture, frailty in elderly population, enhancing immune response and HIV-associated lipodystrophy (U.S. Pat. No. 7,316,997).

In practical terms, it is very important to conserve the physical and chemical integrity of a peptide compound of pharmaceutical interest during its manufacturing process, subsequent handling, storage, and patient use. Loss of biological efficacy and potency has been associated with changes in physical (e.g., aggregation, denaturation, changes in secondary and higher order structures) and chemical (e.g., oxidation, deamidation, isomerization of individual amino acids) integrity.

Some denaturation problems are specific to certain amino acids or certain amino acid sequences such as proteolysis, enzymatic degradation, oxidation, pH-related denaturation, etc.

Therefore, there is a need to provide improved formulations of GRF molecules as well so as to improve retention of its bioactivity after long-term storage.

SUMMARY OF THE INVENTION

The present invention relates to pharmaceutical formulations or compositions of a GRF molecule, methods of preparation thereof, and uses thereof.

In an aspect, the present invention provides a pharmaceutical formulation comprising: a GRF molecule or a pharmaceutically acceptable salt thereof, wherein the GRF molecule comprises a hydrophobic moiety attached to the N-terminus thereof, and a β-cyclodextrin, wherein said formulation has a pH of about 4.5 to about 6.5 and wherein said β-cyclodextrin is not conjugated to said GRF molecule or pharmaceutically acceptable salt thereof.

In an embodiment, the above-mentioned β-cyclodextrin is a modified β-cyclodextrin.

In an embodiment, the above-mentioned the GRF molecule is a GRF analog of formula A:

$$\text{X-GRF Peptide} \quad (A)$$

wherein the GRF peptide is a peptide of formula B:

$$A^1\text{-}A^2\text{-Asp-Ala-Ile-Phe-Thr-Asn-Ser-Tyr-Arg-Lys-}$$
$$A^{13}\text{-Leu-}A^{15}\text{-Gln-Leu-}A^{18}\text{-Ala-Arg-Lys-Leu-}$$
$$\text{Leu-}A^{24}\text{-}A^{25}\text{-Ile-}A^{27}\text{-}A^{28}\text{-Arg-}A^{33}\text{-}R^0 \quad (B)$$

(SEQ ID NO:1)
wherein:
$A^1$ is Tyr or His;
$A^2$ is Val or Ala;
$A^{13}$ is Val or Ile;
$A^{15}$ is Ala or Gly;
$A^{18}$ is Ser or Tyr;
$A^{24}$ is Gln or His;
$A^{25}$ is Asp or Glu;
$A^{27}$ is Met, Ile or Nle
$A^{28}$ is Ser or Asn;
$A^{30}$ is a bond or amino acid sequence of 1 up to 15 residues; and
$R^0$ is $NH_2$ or $NH\text{---}(CH_2)_n\text{---}CONH_2$, with n=1 to 12;
wherein X is a hydrophobic tail anchored via an amide bond to the N-terminus of the peptide, the hydrophobic tail defining a backbone of 5 to 7 atoms, wherein the backbone can be substituted by $C_{1-6}$ alkyl, $C_{3-6}$ cycloalkyl, or $C_{6-12}$ aryl and the backbone comprises at least one rigidifying moiety connected to at least two atoms of the backbone, and wherein said moiety is a double bond, triple bond, saturated or unsaturated $C_{3-9}$ cycloalkyl, or $C_{6-12}$ aryl.

In a further embodiment, X is:

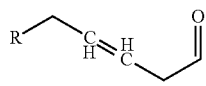

(i)

wherein R is H, $CH_3$ or $CH_2CH_3$, and the double bond is cis or trans;

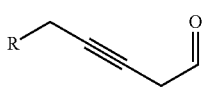

(ii)

wherein R is H, $CH_3$ or $CH_2CH_3$, and the double bond is cis or trans;

(iii)

wherein R is H, $CH_3$ or $CH_2CH_3$, wherein X is in a cis or trans configuration, and wherein said GRF analog is a racemic mixture or a pure enantiomer;

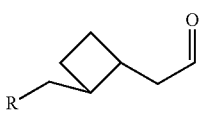

(iv)

wherein R is H, $CH_3$ or $CH_2CH_3$, wherein X is in a cis or trans configuration, and wherein said GRF analog is a racemic mixture or a pure enantiomer;

(v)

wherein R is H, $CH_3$ or $CH_2CH_3$, and wherein when R is $CH_3$ or $CH_2CH_3$, X is in a cis or trans configuration;

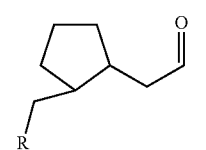

(vi)

wherein R is H, $CH_3$ or $CH_2CH_3$, wherein X is in a cis or trans configuration, and wherein said GRF analog is a racemic mixture or a pure enantiomer;

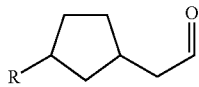

(vii)

wherein R is H, $CH_3$ or $CH_2CH_3$, wherein when R is $CH_3$ or $CH_2CH_3$, X is in a cis or trans configuration, and wherein said GRF analog is a racemic mixture or a pure enantiomer;

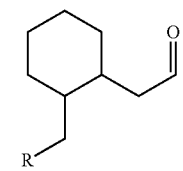

(viii)

wherein R is H, $CH_3$ or $CH_2CH_3$, wherein X is in a cis or trans configuration, and wherein said GRF analog is a racemic mixture or a pure enantiomer;

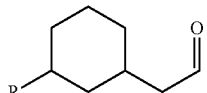

(ix)

wherein R is H, $CH_3$ or $CH_2CH_3$, wherein when R is $CH_3$ or $CH_2CH_3$, X is in a cis or trans configuration, and wherein said GRF analog is a racemic mixture or a pure enantiomer;

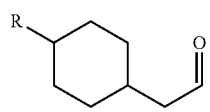

(x)

wherein R is H, $CH_3$ or $CH_2CH_3$, and wherein when R is $CH_3$ or $CH_2CH_3$, X is in a cis or trans configuration;

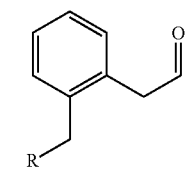

(xi)

wherein R is H, $CH_3$ or $CH_2CH_3$;

(xii)

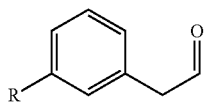

wherein R is H, CH₃ or CH₂CH₃;

(xiii)

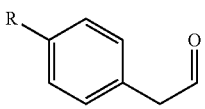

wherein R is H, CH₃ or CH₂CH₃; or (xiv)

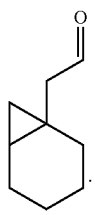

In another embodiment, $A^{30}$ is: (a) a bond; (b) an amino acid sequence corresponding to positions 30-44 of a natural GRF peptide (SEQ ID NO: 6); and (c) said amino acid sequence of SEQ ID NO: 6, having a 1-14 amino acid deletion from its C-terminus.

In an embodiment, the above-mentioned GRF peptide is: (a) a polypeptide comprising the amino acid sequence of SEQ ID NO: 2 or 3; (b) a polypeptide comprising the amino acid sequence of SEQ ID NO: 4 or 5; or (c) said polypeptide of (a) having a 1 to 14 amino acid deletion from its C-terminus.

In a further embodiment, the GRF analog is (hexenoyl trans-3)hGRF(1-44)NH₂ (SEQ ID NO: 7).

In an embodiment, the above-mentioned the formulation is lyophilized or dehydrated. In another embodiment, the above-mentioned formulation is liquid.

In an embodiment, the above-mentioned modified β-cyclodextrin is an alkyl- or hydroxyalkyl-β-cyclodextrin. In a further embodiment, the alkyl- or hydroxyalkyl-β-cyclodextrin is a ($C_1$-$C_6$)alkyl- or hydroxy($C_1$-$C_6$)alkyl-3-cyclodextrin. In a further embodiment, the modified β-cyclodextrin is hydroxypropyl-β-cyclodextrin (HP-β-CD). In another embodiment, the β-cyclodextrin is methyl-3-cyclodextrin (M-β-CD).

In an embodiment, the above-mentioned cyclodextrin is present at a concentration of about 2 to about 15% (w/v), in further embodiments at a concentration of about 2 to about 12.5% (w/v), about 2 to about 10% (w/v), about 2.5 to about 15% (w/v), about 2.5 to about 12.5% (w/v), about 2.5 to about 10% (w/v), about 5 to about 15% (w/v), about 5 to about 12.5% (w/v), about 5 to about 10% (w/v), about 7.5 to about 12.5% (w/v), about 7.5 to about 10% (w/v), or about 5, 7.5, 10, 12.5 or 15% (w/v).

In an embodiment, the above-mentioned formulation has a pH of about 4.5 to about 6.2, in further embodiments about 4.5 to about 6.0, about 4.8 to about 6.5, about 4.8 to about 6.2, about 4.8 to about 6.0, about 5.0 to about 6.5, about 5.0 to about 6.2, 5.0 to about 6.0, about 5.2 to about 6.5, about 5.2 to about 6.2, about 5.2 to about 6.0, about 5.5 to about 6.5, about 5.5 to about 6.2, about 5.5 to about 6.0, about 5.8 to about 6.5, about 5.8 to about 6.2, about 5.8 to about 6.0, or about 5.0, 5.2, 5.5, 5.8, 6.0 or 6.2.

In an embodiment, the above-mentioned formulation is liquid and has a tonicity of about 250 to about 350 mOsm/L.

In an embodiment, the above-mentioned formulation further comprises a bulking agent, in a further embodiment the bulking agent is mannitol, sucrose, glycine, methionine, or a combination thereof. In an embodiment, the bulking agent is present in an amount of up to about 5% (w/v). In an embodiment, the bulking agent is mannitol, in further embodiments the mannitol is present in an amount of about 2.5, 3.5, 4.0, 4.3, 4.7 or 5.0% (w/v).

In an embodiment, the above-mentioned formulation further comprises an anti-microbial agent. In an embodiment, the anti-microbial agent is m-cresol, benzyl alcohol, benzalkonium chloride, phenol or a combination thereof. In a further embodiment, the anti-microbial agent is m-cresol. In a further embodiment, the anti-microbial agent is benzyl alcohol. In an embodiment, the anti-microbial agent is present in an amount of up to about 0.9% (w/v), in further embodiments in an amount of up to about 0.6% (w/v) or up to about 0.3% (w/v). In yet a further embodiment, the anti-microbial agent is present in an amount of about 0.10, 0.15, 0.20, 0.25 or 0.30% (w/v).

In an embodiment, the above-mentioned formulation further comprises a buffer, in a further embodiment a lactate buffer, an acetate buffer, a glutamate buffer, an aspartate buffer, a glycine buffer, or a combination thereof.

In an embodiment, the above-mentioned GRF molecule or pharmaceutically acceptable salt thereof is present in an amount of up to about 8 mg/ml, in further embodiments in an amount of about 4 to about 8 mg/ml, about 6 to about 8 mg/ml, about 1, 2, 3, 4, 5, 6, 7 or 8 mg/ml, more particularly about 6 mg/ml or about 8 mg/ml.

In an embodiment, the above-mentioned formulation comprises: [trans-3-hexenoyl]hGRF (1-44) amide, about 2 to about 10% (w/v) of a modified 3-cyclodextrin, wherein the modified β-cyclodextrin is hydroxypropyl-β-cyclodextrin, methyl-3-cyclodextrin, or a combination thereof, the formulation having a pH of about 5.5 to about 6.0, more particularly 6.0.

In an embodiment, the above-mentioned formulation comprises: [trans-3-hexenoyl]hGHRH (1-44) amide, about 5 to about 10% (w/v) of a modified 3-cyclodextrin, wherein the modified β-cyclodextrin is hydroxypropyl-β-cyclodextrin, methyl-3-cyclodextrin, or a combination thereof, the formulation having a pH of about 5.5 to about 6.0, more particularly 6.0.

In an embodiment, the above-mentioned formulation comprises up to about 5% (w/v) mannitol.

In an embodiment, the above-mentioned formulation comprises about 6 to about 8 mg/ml [trans-3-hexenoyl]hGHRH (1-44) amide.

In an embodiment, at least 70% of the [trans-3-hexenoyl]hGHRH (1-44) amide is not deamidated at $Asn^8$ after 2 years of storage at temperature conditions of about 2° C. to about 8° C. In further embodiments, at least 80%, 85% or 90% of the [trans-3-hexenoyl]hGHRH (1-44) amide is not deamidated at $Asn^8$ after 2 years of storage at temperature conditions of about 2° C. to about 8° C.

In another aspect, the present invention provides a lyophilized or dehydrated pharmaceutical formulation prepared by lyophilizing or dehydrating the above-mentioned pharmaceutical formulation. In an embodiment, the above-mentioned at least 70% of the GRF molecule or [trans-3-hexenoyl]hGRF (1-44) amide is not deamidated at $Asn^8$ after 3 years of storage at temperature conditions of about 15° C. to about 25° C. In further embodiments, at least 80%, 85% or 90% of the GRF molecule or [trans-3-hexenoyl]hGRF (1-44) amide is not deamidated at $Asn^8$ after 3 years of storage at temperature conditions of about 15° C. to about 25° C.

In another aspect, the present invention provides a method for inducing growth hormone secretion in a subject in need thereof, said method comprising administering to said subject an effective amount of (a) the above-mentioned pharmaceutical formulation or (b) a liquid pharmaceutical formulation prepared by suspension of the above-mentioned lyophilized or dehydrated pharmaceutical formulation with a sterile aqueous solution.

In another aspect, the present invention provides the use of (a) the above-mentioned pharmaceutical formulation, or (b) a liquid pharmaceutical formulation prepared by suspension of the above-mentioned lyophilized or dehydrated pharmaceutical formulation with a sterile aqueous solution, for inducing growth hormone secretion in a subject.

In another aspect, the present invention provides the above-mentioned pharmaceutical formulation, or a liquid pharmaceutical formulation prepared by suspension of the above-mentioned lyophilized or dehydrated pharmaceutical formulation with a sterile aqueous solution, for use in inducing growth hormone secretion in a subject.

In an embodiment, the method or use is for the treatment of at least one of HIV-associated lipodystrophy, HIV-lipohypertrophy, abdominal obesity, GH deficiency, frailty, mild cognitive impairment, immune deficiency, wasting associated with a chronic disease or long-term disease, or malnutrition associated with a chronic disease or long-term disease.

In an embodiment, the above-mentioned formulation is administered for, or is for administration at, a daily dose of the GRF molecule or pharmaceutically acceptable salt thereof of about 0.1 mg to about 20 mg.

In an embodiment, the above-mentioned formulation is administered subcutaneously, or is for subcutaneous administration.

In an embodiment, the above-mentioned sterile aqueous solution is sterile water. In an embodiment, the above-mentioned sterile aqueous solution comprises an anti-microbial agent.

In another aspect, the present invention provides a kit comprising the above-mentioned pharmaceutical formulation, in a sterile container.

In another aspect, the present invention provides a kit comprising the above-mentioned lyophilized or dehydrated formulation, in a sterile container.

In an embodiment, the above-mentioned kit further comprises a sterile aqueous solution. In a further embodiment, the sterile aqueous solution comprises an anti-microbial agent, more particularly m-cresol or benzyl alcohol.

In another aspect, the present invention provides a method of preparing a stabilized pharmaceutical formulation of a GRF molecule or a pharmaceutically acceptable salt thereof, wherein the GRF molecule comprises a hydrophobic moiety attached to the N-terminus thereof, the method comprising combining the GRF molecule or a pharmaceutically acceptable salt thereof and a β-cyclodextrin, wherein the β-cyclodextrin is not conjugated to the GRF molecule or pharmaceutically acceptable salt thereof and the pH of the formulation is about 4.5 to about 6.5.

In another aspect, the present invention provides a method of preparing a stabilized liquid pharmaceutical formulation of a GRF molecule or a pharmaceutically acceptable salt thereof, wherein the GRF molecule comprises a hydrophobic moiety attached to the N-terminus thereof, the method comprising: (a) combining the GRF molecule or a pharmaceutically acceptable salt thereof and a β-cyclodextrin in an aqueous solution, wherein the β-cyclodextrin is not conjugated to the GRF molecule or pharmaceutically acceptable salt thereof; and (b) adjusting the pH of the solution to about 4.5 to about 6.5. In an embodiment, the method further comprises lyophilizing or dehydrating the solution after step (b).

In another aspect, the present invention provides a method of stabilizing a GRF molecule or a pharmaceutically acceptable salt thereof, wherein the GRF molecule comprises a hydrophobic moiety attached to the N-terminus thereof, the method comprising combining the GRF molecule or a pharmaceutically acceptable salt thereof with a β-cyclodextrin, wherein the modified β-cyclodextrin is not conjugated to the GRF molecule or pharmaceutically acceptable salt thereof and the pH of the formulation is about 4.5 to about 6.5.

In another aspect, the present invention provides A method of stabilizing a GRF molecule or a pharmaceutically acceptable salt thereof, wherein the GRF molecule comprises a hydrophobic moiety attached to the N-terminus thereof, the method comprising: (a) combining the GRF molecule or a pharmaceutically acceptable salt thereof with a β-cyclodextrin in an aqueous solution, wherein the modified β-cyclodextrin is not conjugated to the GRF molecule or pharmaceutically acceptable salt thereof; and (b) adjusting the pH of the solution to about 4.5 to about 6.5. In an embodiment, the method further comprises lyophilizing or dehydrating the solution after step (b).

In another aspect, the present invention provides a method of inhibiting $Asn^8$ deamidation of a GRF molecule or a pharmaceutically acceptable salt thereof, wherein the GRF molecule comprises a hydrophobic moiety attached to the N-terminus thereof, the method comprising combining the GRF molecule or a pharmaceutically acceptable salt thereof with a β-cyclodextrin, wherein the β-cyclodextrin is not conjugated to the GRF molecule or pharmaceutically acceptable salt thereof, and the pH of the formulation is about 4.5 to about 6.5.

In another aspect, the present invention provides a method of inhibiting $Asn^8$ deamidation of a GRF molecule or a pharmaceutically acceptable salt thereof, wherein the GRF molecule comprises a hydrophobic moiety attached to the N-terminus thereof, the method comprising: (a) combining the GRF molecule or a pharmaceutically acceptable salt thereof with a β-cyclodextrin in an aqueous solution, wherein the β-cyclodextrin is not conjugated to the GRF molecule or pharmaceutically acceptable salt thereof; and (b) adjusting the pH of the solution to about 4.5 to about 6.5. In an embodiment, the method further comprises lyophilizing or dehydrating the solution after step (b).

The liquid pharmaceutical formulation of the present invention is suitable for lyophilization or dehydration and provides a high stability of the GRF molecule when the formulation is stored in a lyophilized, dried or solid form for a long period of time, such as at least 1 week, at least 2 weeks, at least 3 weeks, at least 1 month, at least 2 months, at least 3 months, at least 4 months, at least 6 months, at least 12 months, at least 18 months, at least 24 months, at least 30 months or at least 36 months. The liquid pharmaceutical formulation of the present invention is suitable for lyophilization or dehydration and provides a high stability of the GRF molecule when the formulation is stored in a lyophilized/dried form for a different temperature conditions, such as about 2° C. to about 8° C., about 20° C. to about 25° C. (room temperature), at about 40° C. or less than about 40° C. In an embodiment, the GRF molecule when the formulation is stored in a lyophilized, dried or solid form is stable for at least 24 months or at least 36 months at room temperature, i.e. at about 20° C. to about 25° C.

Other objects, advantages and features of the present invention will become more apparent upon reading of the following non-restrictive description of specific embodiments thereof, given by way of example only with reference to the accompanying drawings.

The present description refers to a number of documents, the content of which is herein incorporated by reference in their entirety.

BRIEF DESCRIPTION OF THE DRAWINGS

In the appended drawings:

FIG. 10 shows differential second-derivative spectra of tesamorelin (8 mg/mL) in the presence of different concentrations of HP-$\beta$-CD (from 0% to 25% (w/v), with 2.5% increment);

FIG. 11 shows signal intensity at 260, 276, and 284 nm in the differential second-derivative spectra of tesamorelin as a function of HP-$\beta$-CD concentration stored at 4° C. over a period of 15 months (RP-HPLC data);

DESCRIPTION OF ILLUSTRATIVE EMBODIMENTS

Figure 1:
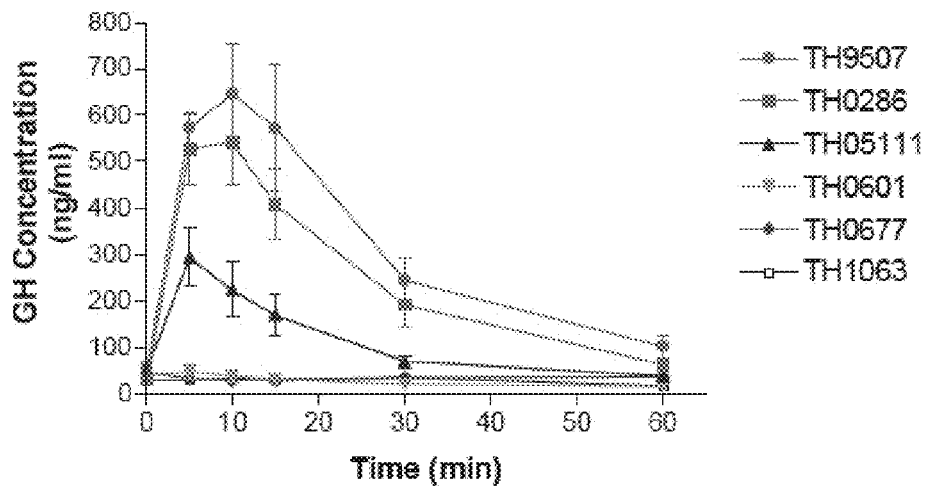
FIG. 1 shows the GH-releasing effect of tesamorelin (TH9507) and its major degradants (as defined below)

The present invention provides pharmaceutical formulations comprising a GRF molecule and more particularly, a GRF analog of formula A described herein. Several formulations of [trans-3-hexenoyl]hGRF (1-44) amide (also referred to herein as tesamorelin or TH9507) have been exemplified and compared herein.

[trans-3-hexenoyl]hGRF (1-44) amide, also referred to herein as tesamorelin or TH9507, has the following structure:
(trans)$CH_3$—$CH_2$—CH=CH—$CH_2$—CO-Tyr-Ala-Asp-
Ala-Ile-Phe-Thr-Asn-Ser-Tyr-Arg-Lys-Val-Leu-Gly-Gln-
Leu-Ser-Ala-Arg-Lys-Leu-Leu-Gln-Asp-Ile-Met-Ser-
Arg-Gln-Gln-Gly-Glu-Ser-Asn-Gln-Glu-Arg-Gly-Ala-
Arg-Ala-Arg-Leu-$NH_2$ (SEQ ID NO: 7).

Degradation of Tesamorelin

The "hot spots" of chemical degradation of tesamorelin are residues $Asp^3$, $Asn^8$, and $Met^{27}$. It has been demonstrated for GRF molecules that deamidation of the $Asn^8$ residue occurs either at acidic pH<2 or slightly basic pHs (Bongers J. Heimer E P, Lambros T, Pan Y C E, Campbell R M, Felix A M. Degradation of aspartic acid and asparagine residues in human growth hormone-releasing factor. Int. *J. Peptide Protein Res.*, 39, 1992, 364-374). There are two principal mechanisms for deamidation of $Asn^8$, depending on the pH conditions. Deamidation at acidic pHs (pH<2) occurs through direct hydrolysis of the side chain amide and is not accompanied by isomerization of the resultant $Asp^8$ residue. Deamidation of $Asn^8$ at pH>5 is known to be accompanied by isomerization to a succinimide intermediate followed by hydrolysis, and results in formation of $\beta$-$Asp^8$ (TH0601) and Asp⁸ (or α-Asp⁸; TH05111) derivatives. As for many other peptides, deamidation proceeds faster at more basic pH.

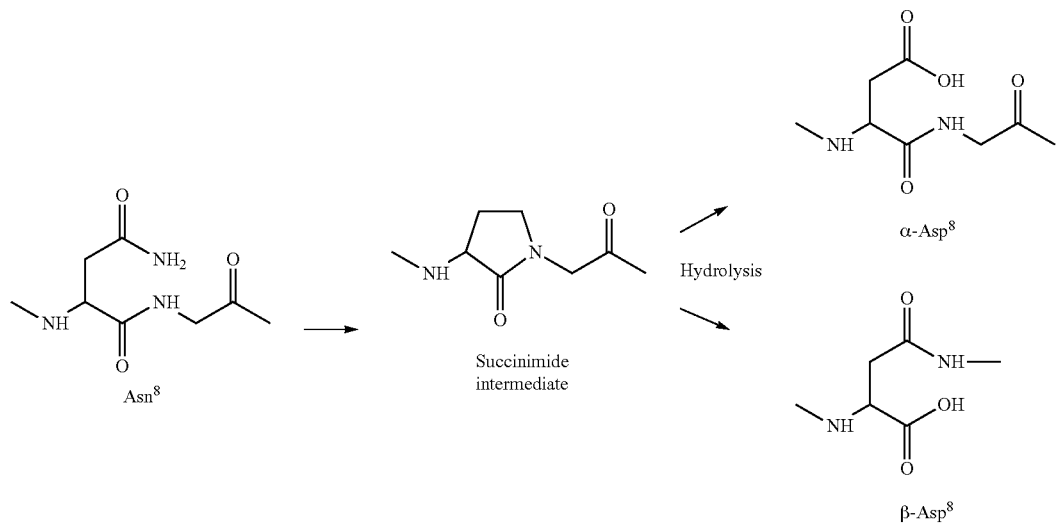

At the same time, slightly acidic pH is known to favor formation of the TH1063 impurity that has been identified as succinimidyl intermediate (cyclic imide in position 3) in the transformation of Asp³ in tesamorelin into β-Asp³ derivative (TH0677):

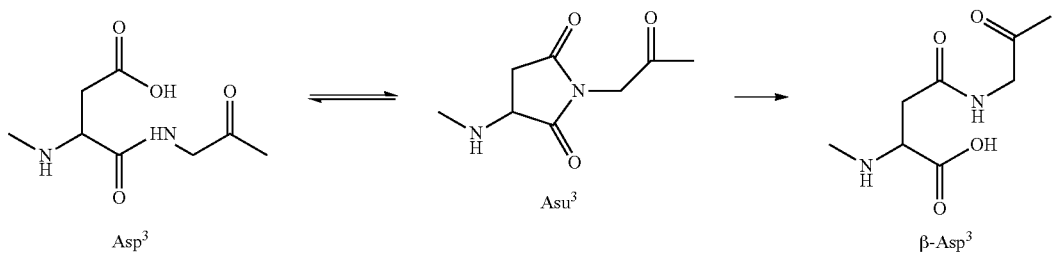

In the studies described herein, various formulations comprising tesamorelin were prepared, and analyzed for stability, notably in respect of the presence of one or more degradation products. The degradation products assessed include one or more of the following:

TH0286: tesamorelin oxidized at Met²⁷;
TH0511: Asp⁸ tesamorelin (i.e., following deamidation of Asn⁸);
TH0601: β-Asp⁸ tesamorelin;
TH0677: β-Asp³ tesamorelin;
TH1063: See Table 1; tesamorelin with cyclic form of Asp³, i.e. Asu³ tesamorelin In an aspect, the present invention provides a pharmaceutical formulation (e.g., liquid or solid) comprising:
a GRF molecule or a pharmaceutically acceptable salt of said molecule, and
a β-cyclodextrin,
wherein the formulation has a pH of about 4.5 to about 6.5 (upon resolubilization/reconstitution in the case of a solid formulation) and wherein the β-cyclodextrin is not conjugated to said GRF molecule or pharmaceutically acceptable salt thereof.

In an embodiment, the GRF molecule comprises a hydrophobic moiety attached to the N-terminus thereof. In an embodiment, the hydrophobic moiety comprises the hydrophobic tail represented by group X described below. In a further embodiment, the hydrophobic moiety consists of the hydrophobic tail represented by group X described below.

β-cyclodextrin is a 7-membered sugar ring molecule, containing seven α-D-glucopyranoside units. It has the following structure:

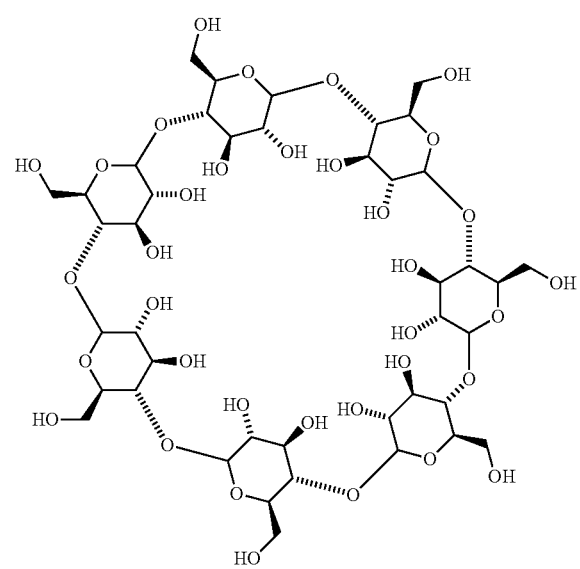

One or more of the hydroxyl groups of one or more of the sugar units may be modified, for example with an alkyl, alkenyl or alkynyl group, or with a substituted alkyl, alkenyl or alkynyl group. Therefore, in embodiments, the β-cyclodextrin may be unmodified or unsubstituted, or may be modified or substituted. As such, in a further embodiment, the β-cyclodextrin is a modified β-cyclodextrin. "Modified β-cyclodextrin" as used herein refers to a β-cyclodextrin that contains a modification at one or more hydroxyl groups of one or more sugar units of the β-cyclodextrin, i.e., a group or moiety that is attached to one or more hydroxyl groups of one or more sugar units of the β-cyclodextrin. As such, in embodiments, the modified β-cyclodextrin is an alkyl-, alkenyl-, alkynyl, substituted alkyl-, substituted alkenyl or substituted alkynyl-β-cyclodextrin (e.g., with a hydroxyl substitution). In embodiments, the alkyl, alkenyl or alkynyl groups are ($C_1$-$C_6$)alkyl, ($C_1$-$C_6$)alkenyl or ($C_1$-$C_6$)alkynyl groups. In a further embodiment, the modified β-cyclodextrin is a ($C_1$-$C_6$) alkyl β-cyclodextrin, in a further embodiment methyl-β-cyclodextrin (M-β-CD). In a further embodiment, the modified β-cyclodextrin is a hydroxy($C_1$-$C_6$)alkyl β-cyclodextrin, in a further embodiment hydroxypropyl-β-cyclodextrin (HP-β-CD).

In the formulations of the present invention, the β-cyclodextrin, which may or may not be modified as noted above, acts as a stabilizer, meaning that it stabilizes the GRF molecule or pharmaceutically acceptable salt thereof against processes that would reduce its activity, in an embodiment against chemical processes, in a further embodiment against the deamidation of $Asn^8$ at pharmaceutically acceptable pHs.

The present invention further provides a method of stabilizing a GRF molecule or a pharmaceutically acceptable salt thereof, comprising the steps of:

(a) combining the GRF molecule or a pharmaceutically acceptable salt thereof with a β-cyclodextrin in an aqueous solution, wherein the β-cyclodextrin is not conjugated to the GRF molecule or pharmaceutically acceptable salt thereof; and (b) adjusting the pH of the solution to about 4.5 to about 6.5.

The present invention further provides a method of inhibiting $Asn^8$ deamidation and isomerization of a GRF molecule or a pharmaceutically acceptable salt thereof, comprising the steps of:

(a) combining the GRF molecule or a pharmaceutically acceptable salt thereof with a β-cyclodextrin in an aqueous solution, wherein the β-cyclodextrin is not conjugated to the GRF molecule or pharmaceutically acceptable salt thereof; and (b) adjusting the pH of the solution to about 4.5 to about 6.5.

The present invention further provides the use of β-cyclodextrin for stabilizing a GRF molecule or a pharmaceutically acceptable salt thereof, wherein the β-cyclodextrin is not conjugated to the GRF molecule or pharmaceutically acceptable salt thereof. In an embodiment, the β-cyclodextrin and the GRF molecule or pharmaceutically acceptable salt thereof are in an aqueous solution at ph 4.5 to about 6.5.

The present invention further provides the use of β-cyclodextrin for inhibiting $Asn^8$ deamidation and isomerization of a GRF molecule or a pharmaceutically acceptable salt thereof, wherein the β-cyclodextrin is not conjugated to the GRF molecule or pharmaceutically acceptable salt thereof. In an embodiment, the β-cyclodextrin and the GRF molecule or pharmaceutically acceptable salt thereof are in an aqueous solution at ph 4.5 to about 6.5.

While the formulations of the invention comprise a GRF molecule or a pharmaceutically acceptable salt thereof and a β-cyclodextrin, the GRF molecule or a pharmaceutically acceptable salt thereof is not conjugated to the β-cyclodextrin, i.e., there is no covalent attachment between the GRF molecule or a pharmaceutically acceptable salt thereof and the β-cyclodextrin.

In an embodiment, the β-cyclodextrin is present in the formulation at a concentration of about 2 to about 15% (w/v), in a further embodiment about 2 to about 12.5% (w/v), in a further embodiment about 2 to about 10% (w/v), in a further embodiment about 2.5 to about 15% (w/v), in a further embodiment about 2.5 to about 12.5% (w/v), in a further embodiment about 2.5 to about 10% (w/v), in a further embodiment about 5 to about 15% (w/v), in a further embodiment about 5 to about 12.5% (w/v), in a further embodiment about 5 to about 10% (w/v), in a further embodiment about 7.5 to about 12.5% (w/v), in a further embodiment about 7.5 to about 10% (w/v), in further embodiments about 5, 7.5, 10, 12.5 or 15% (w/v), in a further embodiment about 10% (w/v).

As used herein, "biologically acceptable" (or "pharmaceutically acceptable") refers to materials characterized by the absence of (or limited) toxic or adverse biological effects in vivo. It refers to those compounds, formulations, formulations and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

The term "formulation" or "pharmaceutical formulation" as used herein refers to preparations which are in such form as to permit the active agents (e.g., a GRF molecule, such as [trans-3-hexenoyl]hGRF (1-44) amide) to be effective, and which contains no additional components which are toxic to the subjects to which the formulation would be administered. It refers to a formulation of the active agents (e.g., a G GRF molecule, such as [trans-3-hexenoyl]hGRF (1-44) amide) and any buffers, bulking agents, adjuvants, carriers, stabilizers, surfactants and such other additives deemed necessary to maintain acceptable levels of activity and stability of the active agents during manufacture, storage, handling, and use. The pharmaceutical formulations of the present invention are suitable for lyophilization and the long-term storage of the active agents (e.g., a GRF molecule, such as [trans-3-hexenoyl]hGRF (1-44) amide) in a lyophilized form.

The term "GRF molecule" as used in the context of the present invention includes, without limitation, human native GRF (1-44) and fragments (1-40), (1-29), fragments ranging between 1-29 and the 1-44 sequence, and any other fragments; GRF from other species and fragments thereof; GRF variants containing amino acid(s) substitution(s), addition(s) and/or deletion(s) such that the amino acid sequence of the variant has at least about 90% of homology with the native amino acid sequence, in an embodiment at least about 95% of homology with the native amino acid sequence. In an embodiment, the above-mentioned fragments/variants retain at least about 10% of the activity of stimulating GH secretion as compared to the native GRF; derivatives or analogs of GRF or fragments or variants thereof having for example an organic or hydrophobic group or a moiety coupled to the GRF amino acid sequence at the N-terminus, the C-terminus or on the side-chain; and salts of GRF (human or from other species), as well as salts of GRF fragments, variants, analogs and derivatives. The GRF molecules of the present invention also encompass the GRF molecules currently known in the art, including, without limitation, the albumin-conjugated GRF (U.S. Pat. No. 7,268,113); pegylated GRF peptide (U.S. Pat. Nos. 7,256,258 and 6,528,485); porcine GHRH (1-40) (U.S. Pat. No. 6,551,996); canine GRF (U.S. patent application no.

2005/0064554); GRF variants of 1-29 to 1-44 amino acid length (U.S. Pat. Nos. 5,846,936, 5,696,089, 5,756,458 and 5,416,073, and U.S. patent application Nos. 2006/0128615 and 2004/0192593); and Pro⁰-GRF peptide and variants thereof (U.S. Pat. No. 5,137,872).

The GRF analogs include those described in U.S. Pat. Nos. 5,681,379 and 5,939,386, which also describe their method of synthesis. More particularly, these GHRH analogs are defined by the following formula A:

X-GRF Peptide (A)

wherein the GHRH peptide is a peptide of the following formula B: A1-A2-Asp-Ala-Ile-Phe-Thr-Asn-Ser-Tyr-Arg-Lys-A13-Leu-A15-Gln-Leu-A18-Ala-Arg-Lys-Leu-Leu-A24-A25-Ile-A27-A28-Arg-A30-R0 (B) (SEQ ID NO: 1) wherein, A1 is Tyr or His;
A2 is Val or Ala;
A13 is Val or Ile;
A15 is Ala or Gly;
A18 is Ser or Tyr;
A24 is Gln or His;
A25 is Asp or Glu;
A27 is Met, Ile or Nle
A28 is Ser or Asn;
A30 is a bond or amino acid sequence of 1 up to 15 residues; and
R0 is $NH_2$ or $NH-(CH_2)_n-CONH_2$, with n=1 to 12.

The group X is a hydrophobic tail anchored via an amide bond to the N-terminus of the peptide, the hydrophobic tail defining a backbone of 5 to 7 atoms. The backbone can be substituted by $C_{1-6}$ alkyl, $C_{3-6}$ cycloalkyl, or $C_{6-12}$ aryl and the backbone comprises at least one rigidifying moiety connected to at least two atoms of the backbone. The rigidifying moiety is a double bond, triple bond, saturated or unsaturated $C_{3-9}$ cycloalkyl, or $C_{6-12}$ aryl.

In an embodiment, group X is:

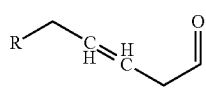
(i)

wherein R is H, $CH_3$ or $CH_2CH_3$, and the double bond is cis or trans;

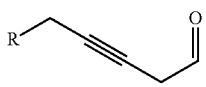
(ii)

wherein R is H, $CH_3$ or $CH_2CH_3$, and the double bond is cis or trans;

(iii)

wherein R is H, $CH_3$ or $CH_2CH_3$, wherein X is in a cis or trans configuration, and wherein said GRF analog is a racemic mixture or a pure enantiomer;

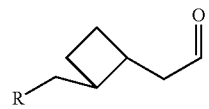
(iv)

wherein R is H, $CH_3$ or $CH_2CH_3$, wherein X is in a cis or trans configuration, and wherein said GRF analog is a racemic mixture or a pure enantiomer;

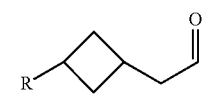
(v)

wherein R is H, $CH_3$ or $CH_2CH_3$, and wherein when R is $CH_3$ or $CH_2CH_3$, X is in a cis or trans configuration;

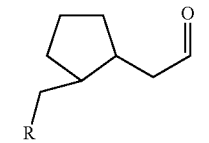
(vi)

wherein R is H, $CH_3$ or $CH_2CH_3$, wherein X is in a cis or trans configuration, and wherein said GRF analog is a racemic mixture or a pure enantiomer;

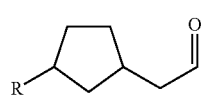
(vii)

wherein R is H, $CH_3$ or $CH_2CH_3$, wherein when R is $CH_3$ or $CH_2CH_3$, X is in a cis or trans configuration, and wherein said GRF analog is a racemic mixture or a pure enantiomer;

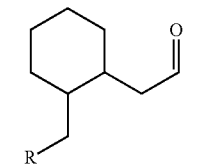
(viii)

wherein R is H, $CH_3$ or $CH_2CH_3$, wherein X is in a cis or trans configuration, and wherein said GRF analog is a racemic mixture or a pure enantiomer;

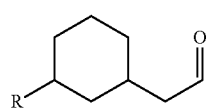
(ix)

wherein R is H, $CH_3$ or $CH_2CH_3$, wherein when R is $CH_3$ or $CH_2CH_3$, X is in a cis or trans configuration, and wherein said GRF analog is a racemic mixture or a pure enantiomer;

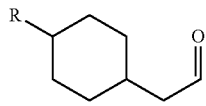

(x)

wherein R is H, CH$_3$ or CH$_2$CH$_3$, and wherein when R is CH$_3$ or CH$_2$CH$_3$, X is in a cis or trans configuration;

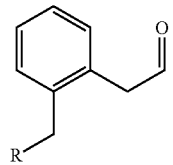

(xi)

wherein R is H, CH$_3$ or CH$_2$CH$_3$;

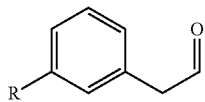

(xii)

wherein R is H, CH$_3$ or CH$_2$CH$_3$;

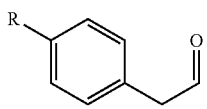

(xiii)

wherein R is H, CH$_3$ or CH$_2$CH$_3$; or

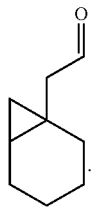

(xiv)

In an embodiment, in formula B, A30 is:
(a) a bond;
(b) an amino acid sequence corresponding to positions 30-44 of a natural GRF peptide (SEQ ID NO: 6), or
(c) the amino acid sequence of (b) (SEQ ID NO: 6) having a 1-14 amino acid deletion from its C-terminus.

In an embodiment, the GRF peptide is:
(a) a polypeptide comprising the amino acid sequence of SEQ ID NO: 2 or 3;
(b) a polypeptide comprising the amino acid sequence of SEQ ID NO: 4 or 5; or
(c) the polypeptide of (a) having a 1 to 14 amino acid deletion from its C-terminus.

In an embodiment, the GRF peptide is:
(a) a polypeptide having the amino acid sequence of SEQ ID NO: 2 or 3;
(b) a polypeptide having the amino acid sequence of SEQ ID NO: 4 or 5; or
(c) the polypeptide of (a) having a 1 to 14 amino acid deletion from its C-terminus.

In an embodiment, the GRF molecule is (hexenoyl trans-3)hGHRH(1-44)NH$_2$ (SEQ ID NO: 7). [trans-3-hexenoyl]hGHRH (1-44) amide (also referred to herein as (hexenoyl trans-3)hGRF(1-44)NH$_2$, tesamorelin or TH9507) is a synthetic human growth hormone releasing factor analog that comprises the 44-amino acid sequence of human growth hormone releasing factor (hGRF) on which a hexenoyl moiety, a C$_6$ side chain, has been anchored on Tyr1 at the N-terminus. [trans-3-hexenoyl]hGHRH (1-44) amide has the following structure:

(trans)CH$_3$—CH$_2$—CH═CH—CH$_2$—CO-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH$_2$ (SEQ ID NO: 7).

The term "solid" as used herein in the context of a formulation of the invention refers to the formulation in a form which is substantially free of moisture, e.g., a solid (e.g., powder) form. Such a solid formulation may be prepared by any method of moisture removal, e.g., by lyophilization, dehydration, or other drying methods or methods to remove water.

The term "suspension" as used herein is intended to refer to suspension, resuspension, reconstitution and/or solubilisation depending on the context. For a matter of consistency, the term "suspension" is used herein to generally refer to the addition of a suitable liquid to a solid formulation.

The term "bulking agent" as used herein refers to a compound used to provide an adequate or desired tonicity of the liquid formulation or of the solution resulting from the suspension of the solid or lyophilized formulation. Preferably, the adequate or desired tonicity of the solution is equal to or approximates isotonicity with physiological fluid of the subject to which the solution is administered. For example, in an embodiment, the formulation or solution has a tonicity of about 250 to about 350 mOsm/L, in further embodiments about 275 to about 325 mOsm/L, about 290 to about 310 mOsm/L, or about 300 mOsm/L. For example, one or more sugars may be used as the bulking agent. Sugars, as used herein, include, but are not limited to, monosaccharides, oligosaccharides and polysaccharides. Examples of suitable sugars include, but are not limited to, mannose, sorbose, xylose, maltose, lactose, sucrose, and dextran. Sugar also includes sugar alcohols, such as mannitol, inositol, dulcitol, xylitol and arabitol. Mixtures of sugars may also be used in accordance with this invention. In an embodiment, the bulking agent is mannitol. Further, one or more amino acids, such as glycine or methionine, may be used as the bulking agent. Various combinations of the above may also be used as the bulking agent. In an embodiment, the bulking agent is present in the formulation at a concentration of up to 10% (w/v). In a further embodiment, the bulking agent is at concentration of about 1 to about 10% (w/v) in the formulation. In a further embodiment, the bulking agent is at concentration of up to about 5% (w/v) in the formulation. In a further embodiment, the bulking agent is at concentration of about 1 to about 5% (w/v) in the formulation. In an embodiment, the bulking agent is in concentration of about 2.5 to about 5% (w/v). In a further embodiment, the bulking agent is in concentration of about 2.5, 3.5, 4.0, 4.3, 4.7 or 5.0% (w/v).

In an embodiment, the pharmaceutical formulations of the present invention have a pharmaceutically acceptable pH of about 4.0 to about 7.5. In a further embodiment, the pharmaceutical formulations of the present invention have a pH of about 4.0 to about 7.0. In a further embodiment, the pharmaceutical formulations of the present invention have a pH of about 4.5 to about 6.5. In a further embodiment, the pharmaceutical formulations of the present invention have a pH of about 4.5 to about 6.2. In a further embodiment, the pharmaceutical formulations of the present invention have a pH of about 4.5 to about 6.0. In a further embodiment, the pharmaceutical formulations of the present invention have a pH of about 4.8 to about 6.5. In a further embodiment, the pharmaceutical formulations of the present invention have a pH of about 4.8 to about 6.2. In a further embodiment, the pharmaceutical formulations of the present invention have a pH of about 4.8 to about 6.0. In a further embodiment, the pharmaceutical formulations of the present invention have a pH of about 5.0 to about 6.5. In a further embodiment, the pharmaceutical formulations of the present invention have a pH of about 5.0 to about 6.2. In a further embodiment, the pharmaceutical formulations of the present invention have a pH of about 5.0 to about 6.0. In a further embodiment, the pharmaceutical formulations of the present invention have a pH of about 5.2 to about 6.5. In a further embodiment, the pharmaceutical formulations of the present invention have a pH of about 5.2 to about 6.2. In a further embodiment, the pharmaceutical formulations of the present invention have a pH of about 5.2 to about 6.0. In a further embodiment, the pharmaceutical formulations of the present invention have a pH of about 5.5 to about 6.5. In a further embodiment, the pharmaceutical formulations of the present invention have a pH of about 5.5 to about 6.2. In a further embodiment, the pharmaceutical formulations of the present invention have a pH of about 5.5 to about 6.0. In a further embodiment, the pharmaceutical formulations of the present invention have a pH of about 5.8 to about 6.5. In a further embodiment, the pharmaceutical formulations of the present invention have a pH of about 5.8 to about 6.2. In a further embodiment, the pharmaceutical formulations of the present invention have a pH of about 5.8 to about 6.0, in a further embodiment about 5.9 to about 6.1. In a further embodiment, the pharmaceutical formulations of the present invention have a pH of about 5.0, 5.2, 5.5, 5.8, 6.0 or 6.2. In a further embodiment, the pharmaceutical formulations of the present invention have a pH of about 6.0.

In an embodiment, the formulations of the present invention further comprise an anti-microbial agent. "Anti-microbial agent" as used herein refers to one or more agents capable of killing or inhibiting the growth of microorganisms (such as bacteria, fungi and protozoans). An anti-microbial agent may be selective (e.g. for a particular type of microorganism) or non-selective (with activity against a broad range of microorganisms). Combinations or anti-microbial agents may also be used in the formulations of the present invention. In embodiments, the anti-microbial agent is m-cresol, benzyl alcohol, or a combination thereof. In an embodiment, the anti-microbial agent is present in the formulation at a concentration of up to about 0.9% (w/v), in a further embodiment up to about 0.6% (w/v), in a further embodiment up to about 0.3% (w/v), in further embodiments at a concentration of about 0.10, 0.15, 0.20, 0.25 or 0.30% (w/v).

In an embodiment, the formulations of the present invention further comprise a buffer. The suitable amount of buffer will vary depending on the type of buffer used and its buffering capacity. The buffer should be of a type appropriate to and present in the formulation in an amount sufficient to maintain the final pH of the formulation in the pH range mentioned above. In embodiments, the buffer is a lactate buffer, an acetate buffer, a glutamate buffer, an aspartate buffer, a glycine buffer, or a combination thereof. In an embodiment, the concentration of buffer in the pharmaceutical formulations of the invention is from about 0.1 mM to about 50 mM. In another embodiment, the concentration of buffer in the pharmaceutical formulations of the invention is from about 1 mM to about 30 mM. In a further embodiment, the concentration of buffer in the pharmaceutical formulations of the invention is from about 5 mM to about 20 mM. In a further embodiment, the concentration of buffer in the pharmaceutical formulations of the invention is about 5, 10, 15, 20, 25, 30, 35, 40, 45 or 50 mM.

The amount of active principal ingredient (e.g., a GRF molecule, such as [trans-3-hexenoyl]hGRF (1-44) amide) contained in pharmaceutical formulations of the present invention can be determined depending on the nature and/or severity of the disease to be treated, the characteristics of the patient (age, weight, etc.) and other factors. Generally, the pharmaceutical formulation of the invention comprises about 1 to about 40 000 µg/ml of active principal ingredient (e.g., a GRF molecule, such as [trans-3-hexenoyl]hGRF (1-44) amide). In an embodiment, the pharmaceutical formulation of the invention comprises about 1000 to about 8000 µg/ml (about 0.099% to about 0.792% by weight) of active principal ingredient (e.g., a GRF molecule, such as [trans-3-hexenoyl] hGHRH (1-44) amide). In another embodiment, the pharmaceutical formulation of the invention comprises about 1000 to about 4000 µg/ml (about 0.099% to about 0.396% by weight) of active principal ingredient (e.g., a GRF molecule, such as [trans-3-hexenoyl]hGRF (1-44) amide). In a further embodiment, the pharmaceutical formulation of the invention comprises about 1000 µg/ml (about 0.099% by weight) of active principal ingredient (e.g., a GRF molecule, such as [trans-3-hexenoyl]hGRF (1-44) amide). In another embodiment, the pharmaceutical formulation of the invention comprises about 4000 µg/ml (about 0.396% by weight) of active principal ingredient (e.g., a GRF molecule, such as [trans-3-hexenoyl] hGRF (1-44) amide). In embodiments, the formulation comprises the active principal ingredient (e.g., a GRF molecule, such as [trans-3-hexenoyl]hGRF (1-44) amide) at a concentration greater than or equal to about 1 mg/ml; in a further embodiment up to about 20 mg/ml, in a further embodiment up to about 8 mg/ml, in a further embodiment from about 1 mg/ml to about 20 mg/ml, in a further embodiment from about 1 mg/ml to about 8 mg/ml, in a further embodiment from about 4 mg/ml to about 8 mg/ml, in a further embodiment from about 6 mg/ml to about 8 mg/ml, in further embodiments at a concentration of about 1, 2, 4, 6, 8, 10, 12, 14, 16, 18 or 20 mg/ml, in a further embodiment about 6 mg/ml, in a further embodiment about 8 mg/ml. In embodiments, the formulation comprises an amount of the active principal ingredient (e.g., a GRF molecule, such as [trans-3-hexenoyl]hGRF (1-44) amide) to effect administration of a dose of the active principal ingredient (e.g., a GRF molecule, such as [trans-3-hexenoyl]hGRF (1-44) amide which is greater than or equal to about 1 mg; in a further embodiment greater than or equal to about 2 mg, in a further embodiment from about 1 mg to about 4 mg, in a further embodiment from about 2 mg to about 4 mg; in a further embodiment, about 1, 2, 3 or 4 mg.

The pharmaceutical formulations of the present invention may further contain diluents, solubilizing agents, excipients, pH-modifiers, soothing agents, buffers, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, methionine and sulfhydryl-containing compounds such as thioalkanoic acid having 1 to 7 carbon atoms. Antioxidants include methionine, erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate, sodium metaphosphate. Other components commonly added may also be contained, e.g., inorganic salts such as sodium chloride, potassium chloride, calcium chloride, sodium phosphate, potassium phosphate, sodium bicarbonate; and organic salts such as sodium citrate, potassium citrate, sodium acetate.

A stable formulation is one in which the active principal ingredient, i.e. the GRF molecule (e.g., [trans-3-hexenoyl] hGRF (1-44) amide) therein essentially retains its physical and chemical stability and integrity upon storage. Various analytical techniques for measuring protein or peptide stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. For rapid screening, the formulation may be kept, for example, at about 40° C. for 2 weeks to 1 month (and for up to 6 months), at which time stability is measured. The formulation may also be kept, for example, at about 2° C. to about 8° C. (e.g., about 4 or 5° C.) or in ambient room temperature conditions (about 15° C. to about 30° C., preferably about 20° C. to about 25° C.) for at least 6 months, at which time stability is measured. The formulation of the present invention offers a better stability of the GRF molecule in its liquid or solid form and is also suitable for preserving the stability of the GHRH molecule in solid or lyophilized form for a period of storage at elevated temperature (e.g., about 40° C.), at room temperature (e.g., about 15-30° C., in a further embodiment about 15-25° C., in a further embodiment about 20-25° C., in a further embodiment about 25° C.), at refrigerated temperature (e.g., about 2° C. to about 8° C., in a further embodiment about 4 or 5° C.). The period of storage may for example be expressed in weeks, months or years, and may be at least 1 week, at least 2 weeks, at least 4 weeks, at least 6 weeks, at least 8 weeks, at least 3 months, at least 4 months, at least 6 months, at least 1 year, at least 18 months, at least 2 years, at least 30 months, or at least 3 years. For example, a "stable" formulation may be one wherein more than about 80%, more than about 90%, more than about 95%, more than about 96%, more than about 97%, more than about 98%, or more than about 99% of the non-degraded active agent is present in the formulation. The stability of the formulations of the present invention may be measured using RP-HPLC (e.g., see Examples below). A "stabilizing effective amount or concentration" as used herein is meant to designate an amount or concentration effective to obtain a stable formulation wherein more than about 80%, more than about 90%, more than about 95%, more than about 96%, more than about 97%, more than about 98%, or more than about 99% of the non-degraded active agent is present in the formulation.

In an embodiment, stability may be characterized in terms of deamidation, or lack thereof, of $Asn^8$ of the GRF molecule. As such, in embodiments, the liquid formulation or composition of the invention comprises a GRF molecule or pharmaceutically acceptable salt thereof, wherein in embodiments at least about 60%, 65%, 70%, 75%, 80%, 85%, 86%, 87%, 88%, 89% or 90% of the GRF molecule is not deamidated at $Asn^8$ after 2 years of storage at refrigerated temperature conditions (i.e. about 2 to about 8° C., in a further embodiment about 4 or 5° C.). In further embodiments, the lyophilized or dehydrated formulation or composition of the invention comprises a GRF molecule or pharmaceutically acceptable salt thereof, wherein in embodiments at least about 60%, 65%, 70%, 75%, 80%, 85%, 86%, 87%, 88%, 89%, 90%, 91%, 92%, 93%, 94% or 95% of the GRF molecule is not deamidated at $Asn^8$ after 3 years of storage at room temperature conditions (about 15° C. to about 30° C., in a further embodiment about 15° C. to about 25° C., in a further embodiment about 20° C. to about 25° C., in a further embodiment about 25° C.).

In further embodiments, the lyophilized or dehydrated formulation or composition of the invention comprises a GRF molecule or pharmaceutically acceptable salt thereof, wherein in embodiments at least about 60%, 65%, 70%, 75%, 80%, 85%, 86%, 87%, 88%, 89%, 90%, 91%, 92%, 93%, 94% or 95% of the GRF molecule is not deamidated at $Asn^8$ after 3 years of storage at room temperature conditions (about 15° C. to about 30° C., followed by reconstitution and 2-weeks storage at 15° C. to about 25° C., in a further embodiment about 20° C. to about 25° C., in a further embodiment about 25° C.)

In further embodiments, the liquid formulation or composition of the invention comprises a GRF molecule or pharmaceutically acceptable salt thereof, wherein in embodiments not more than about 40%, 35%, 30%, 25%, 20%, 15%, 14%, 13%, 12%, 11%, 10%, 9%, 8%, 7%, 6%, 5% or 4% of the GRF molecule is deamidated at $Asn^8$ after 2 years of storage at refrigerated temperature conditions (i.e. about 2 to about 8° C., in a further embodiment about 4 or 5° C.). In further embodiments, the lyophilized or dehydrated formulation or composition of the invention comprises a GRF molecule or pharmaceutically acceptable salt thereof, wherein in embodiments not more than about 40%, 35%, 30%, 25%, 20%, 15%, 14%, 13%, 12%, 11%, 10%, 9%, 8%, 7%, 6% or 5% of the GRF molecule is deamidated at $Asn^8$ after 3 years of storage at room temperature conditions (about 15° C. to about 30° C., in a further embodiment about 15° C. to about 25° C., in a further embodiment about 20° C. to about 25° C., in a further embodiment about 25° C.).

The formulations or compositions of the invention may be useful for inducing or stimulating the secretion of GH in a subject.

Accordingly, in another aspect, the present invention provides a method for inducing or increasing growth hormone secretion in a subject in need thereof, said method comprising administering to said subject an effective amount of the above-mentioned formulation or composition.

In another aspect, the present invention provides a use of the above-mentioned formulation or composition, for inducing or increasing growth hormone secretion in a subject.

In another aspect, the present invention provides a use of the above-mentioned formulation or composition, for the preparation of a medicament for inducing or increasing growth hormone secretion in a subject.

In another aspect, the present invention provides the above-mentioned formulation or composition, for the preparation of a medicament for inducing or increasing growth hormone secretion in a subject.

In another aspect, the present invention provides the above-mentioned formulation or composition, for use in inducing or increasing growth hormone secretion in a subject.

The terms "stimulating," "increasing," or "inducing" or any variations of these terms as used herein, refer to a measurable increase of a biological activity. In embodiments, the increase is at least a 10%, 20%, 40%, 60%, 80%, 90%, 95%, 100% (2-fold), 200% (3-fold) increase in the biological activity relative to a control. For example, a GRF analog is found to stimulate GHRHr activity when an increase in GH levels is measured following administration of the GRF analog to a subject (e.g., animal, human) in comparison to a subject not administered with the GRF analog.

In view of their GHRHr agonist activity and GH-releasing properties, the formulations or compositions of the invention may be useful as a medicament, for prophylactic and/or therapeutic applications in which stimulation of GH/IGF-1 secretion is desirable, for example for the treatment or prevention of conditions/disorders/diseases associated with GRF and/or GH function (e.g., in which reduced GH and/or GHRH function is involved in the etiology of the disease/disorder). Diseases and conditions in which administration of GH, GRF or GRF analogs/derivatives may be beneficial have been extensively described in the art (see, e.g., WO 2009/009727, WO 2006/042408, WO 2005/037307, WO 2004/105789). Such conditions/disorders/diseases include, for example, syndromes associated with fat accumulation, hypercholesterolemia, obesity, syndrome X, lipohypertrophy, lipoatrophy, lipodystrophy (e.g., HIV-associated lipodystrophy syndrome), impaired cognitive function, impaired daytime vigilance, declined function of the immune system (e.g., immunodeficiencies such as T-cell deficiencies), muscle protein catabolism, diseases/conditions associated with muscle wasting such as sarcopenia, frailty, radiotherapy- and/or chemotherapy-related side effects (e.g., in HIV-infected and cancer patients), cachexia (e.g., in cancer patients), hypothalamic pituitary dwarfism, burns, osteoporosis, renal failure, non-union bone fracture, acute/chronic debilitating illness or infection, wound healing, post-surgical problems, lactation failure, infertility in women, neurodegenerative conditions, GRF receptor-dependent tumors, conditions related to aging, sleep disorders/impairment.

Therefore, in other aspects, the present invention provides a method for (1) stimulating daytime vigilance and/or cognitive function, e.g. in conditions related to aging, mild cognitive impairment (MCI), pre-Alzheimer's symptoms (Pre-Onset Alzheimer's), dementia and/or sleep impairment (e.g., age-related sleep impairment), (2) improving/preventing/treating metabolic conditions associated with fat accumulation and/or hypercholesterolemia (obesity, abdominal obesity/adiposity, abdominal obesity with metabolic disorders, abdominal obesity with relative GH deficiency, metabolic syndrome or syndrome X, lipohypertrophy, lipoatrophy, lipodystrophy (e.g., HIV-associated lipodystrophy syndrome), dyslipidemia, hypertriglyceridemia), (3) improving anabolism in catabolic/wasting conditions, such as those observed in acute or chronic renal failure (e.g., acute or chronic renal failure wasting), chronic heart failure (e.g., chronic heart failure wasting), chronic obstructive pulmonary disease (COPD), cystic fibrosis (e.g., cystic fibrosis wasting in adults), frailty, burns, infections (sepsis), muscular dystrophy, congestive heart failure, neurodegenerative conditions (Alzheimer's, pre-Alzheimer's syndromes, amyotrophic lateral sclerosis (ALS), AIDS, protein malnutrition following long-term corticosteroid therapy, following non-union bone fracture, hip fracture, trauma, or major surgery (post-surgical problems), osteoporosis, long-term immobilization, cancer-related cachexia, sarcopenia (e.g., age-related sarcopenia), GI malabsorption (Short Bowel Syndrome (SBS), Crohn's disease) particularly in elderly subjects, for example to increase muscle mass and/or function, (4) improving immune function or reconstitution of immunodeficient states (e.g., T-cell immunodeficiencies) such as that associated aging, HIV infection/AIDS or following high-dose chemotherapy and/or radiotherapy (in HIV-infected and cancer patients), (5) altering a lipid parameter ((a) decreasing cholesterol; (b) decreasing non-HDL cholesterol; (c) decreasing triglycerides; and/or (d) decreasing the ratio of total cholesterol/HDL cholesterol); (6) altering a body composition parameter ((a) increasing lean body mass; (b) decreasing trunk fat; (c) decreasing visceral fat; (d) decreasing abdominal girth; (e) decreasing visceral adipose tissue (VAT); and/or (f) decreasing the VAT/subcutaneous adipose tissue (SAT) ratio), (7) enhancing fertility or treating infertility (in women), treating lactation failure, (8) treating GH deficiency (e.g., GH deficiency with abdominal obesity), providing GH replacement therapy, e.g., in adults, treating idiopathic short stature (ISS) (9) treating GRF receptor-related tumors, (10) treating hypothalamic pituitary dwarfism, (11) improving wound healing, (12) treating burns, (13) treating acute/chronic debilitating illness or infection, and/or (14) preventing/treating a condition characterized by deficient or decreased bone formation (e.g., osteoporosis); the method comprising administering an effective amount of the above-mentioned formulation or composition, to a subject in need thereof.

In other aspects, the present invention provides a use of the above-mentioned formulation or composition comprising the above-mentioned GRF molecule or a pharmaceutically acceptable salt thereof, for improving, preventing and/or treating the conditions, diseases or disorders noted above, or for the preparation/manufacture of a medicament for improving, preventing and/or treating the conditions, diseases or disorders noted above. In other aspects, the present invention provides the above-mentioned formulation or composition comprising the above-mentioned GRF molecule or pharmaceutically acceptable salt thereof for use in improving, preventing and/or treating the conditions, diseases or disorders noted above, or for the preparation/manufacture of a medicament for improving, preventing and/or treating the conditions, diseases or disorders noted above.

The term "treatment" or "treating" as used herein, is defined as the application or administration of the above-mentioned formulation or composition to a subject, who has a disorder, a disease, a symptom of disorder or disease, with the purpose to cure, heal, alleviate, relieve, alter, remedy, ameliorate, improve, reduce the progression or affect the disorder/disease and/or the symptoms of disorder/disease. In an embodiment, the treatment results in no or substantially no effect on blood glucose control (e.g., no clinically significant effects).

The term "prevention" or "preventing" as used herein, is defined as the application or administration of the above-mentioned formulation or composition to a subject, who has a predisposition toward a disorder/disease or who is at risk of developing the disorder/disease, with the purpose to prevent or delay the onset of the disease/disorder or of the symptoms, or reduce the severity of the disease/disorder or of the symptoms, when administered prior to the onset/appearance of the disease/disorder or of the symptoms.

An "effective amount" refers to an amount effective, at dosages and for periods of time necessary, to achieve the desired biological activity (e.g. inducing GH secretion) and/or the prophylactic/therapeutic result (e.g., prevention and/or treatment of the diseases/disorders noted above). A "therapeutically effective amount" refers to an effective amount in the context of therapy; a "prophylactically effective amount" refers to an effective amount in the context of prophylaxis. An effective amount of a compound of the invention may vary according to factors such as the disease state, age, sex, and weight of the individual, and the ability of the compound to elicit a desired response in the individual. Dosage regimens may be adjusted to provide the optimum prophylactic/therapeutic response. An effective amount is also one in which any toxic or detrimental effects of the compound are outweighed by the prophylactic/therapeutic beneficial effects. For any particular subject, specific dosage regimens may be adjusted over time according to the individual need and the professional judgment of the person administering or supervising the administration of the compositions. In an embodiment, the GRF analog is administered at a daily dose of about 0.01 mg to about 30 mg, in a further embodiment of about 0.1 mg to about 20 or 25 mg, in a further embodiment of about 0.5 mg to about 20 mg, in a further embodiment at a daily dose of about 1 mg to about 20 mg.

The formulation or composition of the present invention may be administered, or may be for administration, by any conventional route, such as intravenous, oral, transdermal, intraperitoneal, subcutaneous, mucosal, intramuscular, intranasal, intrapulmonary, parenteral or topical. In an embodiment, the formulation or composition is administered or is for administration by a subcutaneous route.

In an embodiment, the above-mentioned prevention and/or treatment comprises administration of the above-mentioned formulation or composition, in combination with one or more additional active/therapeutic agents. The combination of prophylactic/therapeutic agents and/or compositions may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) of the present invention is used/administered in combination with one or more agent(s) currently used to prevent or treat the disorder in question.

As used herein, the terms "subject" or "patient" are taken to mean warm blooded animals such as mammals, for example, cats, dogs, mice, guinea pigs, horses, bovine cows, sheep and humans. In an embodiment, the subject is a mammal. In a further embodiment, the above-mentioned subject is a human.

The invention further provides a method to prepare the formulations or compositions described herein. The method comprises formulating or combining together (e.g., dissolving, mixing) the ingredients under conditions to obtain the desired formulation (e.g., with respect to formulation, concentration, pH, etc.). For example, with respect to pH, the pH of the formulation may be determined and adjusted accordingly (if necessary) to be within the desired range.

In an aspect, the present invention provides a method of preparing a stabilized pharmaceutical formulation of a GRF molecule or a pharmaceutically acceptable salt thereof, comprising the steps of:

(a) combining the GRF molecule or a pharmaceutically acceptable salt thereof and a modified β-cyclodextrin in an aqueous solution, wherein the modified β-cyclodextrin is not conjugated to the GRF molecule or pharmaceutically acceptable salt thereof; and (b) adjusting the pH of the solution to about 4.5 to about 6.5.

In an embodiment, the solution may subsequently be dehydrated or lyophilized to obtain a solid formulation, which may subsequently be reconstituted.

As used in the specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps. The term "about" is used to indicate that a value includes an inherent variation of error for the device or the method being employed to determine the value, and may include for example a variation of 10%. Where a value is explicitly recited, it is to be understood that values which are about the same quantity or amount as the recited value are also within the scope of the present disclosure, as are ranges based thereon. Use of the singular forms "a," "an," and "the" include plural references unless the context clearly dictates otherwise.

The present invention is illustrated in further details by the following non-limiting examples.

EXAMPLES

Example 1

Materials and Methods

Synthesis of [trans-3-hexenoyl]hGHRH (1-44) amide and Related Substances

[trans-3-hexenoyl]hGHRH (1-44) amide, also referred to herein as tesamorelin or TH9507, as well as related substances TH0286, TH0601, TH0677, and TH05111, are synthesized using FMOC solid phase peptide synthesis starting with Ramage Tricyclic Amide Resin. Protected amino acids and trans-3-hexenoyl acid are used for coupling whereby each protected amino acid and trans-3-hexenoyl acid is dissolved in aluminum oxide-treated DMF with TBTU as a coupling agent and DIPEA to promote activation before coupling. Completeness of couplings is monitored by the Kaiser ninhydrin test (E. Kaiser et al. Anal. Biochem. "Color Test for Detection of Free Terminal Amino Groups in the Solid Phase Synthesis of Peptides") and the TNBS test (Means and Feeney, 1971, Holden-Day Inc. San Francisco "Chemical Modification of Proteins" p. 217).

The side chain protecting groups and the peptide-resin bond are cleaved by stirring the protected peptide-resin in a cleavage cocktail consisting of 90% TFA, 5% EDT and 5% water. The crude peptide is purified by HPLC through a three-stage purification scheme using the following buffers, 0.1% MSA, TEAP pH 6.5, ammonium acetate and 2% HOAc affording pure peptides. The purified peptide lots are pooled and reconstituted in 0.5% acetic acid and lyophilized. The $Asu^3$ derivative, i.e. TH1063, is isolated by cation-exchange chromatography from the solution of TH9507 incubated at pH4 for 3 weeks at 40° C.

Lyophilization Process.

The samples are lyophilized by freezing at −50° C. and holding, primary drying at −10° C. under 100 mTorr and secondary drying at 25° C. under 100 mTorr.

Example 2

Characterization of Activity of Tesamorelin Impurities

TH9507 (tesamorelin) impurities, TH0286, TH05111, TH0601, TH0677 and TH1063, were characterized in terms of their potency and efficacy in a reporter gene assay as well as their GH response in female Sprague Dawley Rats. The reporter gene assay was performed on baby hamster kidney (BHK) cells stably expressing the human GRF receptor and a cAMP-inducible alkaline phosphatase reporter gene; the peptides were tested at concentrations from 1 pM to 10 µM. Acute GH response was measured in blood samples obtained from female rats that were injected with 10 µg/rat peptides in 5% mannitol.

The EC50s of TH0286, TH05111 and TH1063 were comparable to TH9507. B-Asp peptides (TH0601 and TH0677) were less potent with $EC_{50}$s that were 500 and 71 fold higher than TH9507, respectively.

TH0677 and TH1063 did not produce GH in rats; TH0286, TH05111 and TH0601 stimulated GH with $AUC_{(0-60\ min)}$ of 1.3, 2.9 and 12.4 fold lower than TH9507 and $C_{max}$ of 1.2, 2.2 and 14.0 fold lower than TH9507.

In conclusion, β-Asp peptides (TH0601 and TH0677) were less potent in vitro and less active in vivo. TH1063 was completely inactive in vivo.

TH9507 stability studies showed the formation of some impurities due to aspartate cyclization and methionine oxidation. The in vitro and in vivo bioactivity of these oxidation products of TH9507 were characterized in cells and in animals.

Rat Studies.

Sprague-Dawley rats (female, 250-300 g) were obtained from Charles River Inc. The animals were kept in groups of 4 rats per cage and were maintained on standard laboratory chow in 12:12 light:dark cycle.

On the day of the experiment, the animals were anesthetized with 2.5% isoflurane. A mid-section opening was made in the neck to expose the carotid artery. The carotid artery was cannulated with polypropylene tube (PE-50) for blood withdrawal. The rats were subcutaneously injected with the peptides (10 µg/rat) dissolved in formulation 5 (20 mM Sodium Acetate, 5% D-mannitol pH 5 (adjusted with AcOH). Blood samples (400 µL) were collected at pre-dose and at 5, 10, 15, 30 and 60 minutes after the injection into microtainer tubes containing $K_3$EDTA and 25 µl of acidified Hank's buffered salt solution (AHBSS). The samples were immediately centrifuged in a microfuge for 2 minutes and the plasma was collected into screwcap Eppendorf™ tubes and quickly frozen in liquid nitrogen. The samples were kept at −80° C.

GH ELISA.

Rat plasma samples were thawed on ice, vortexed briefly to mix the contents and centrifuged at 9,000 RPM for 2 min at 4° C. GH levels were determined using the Rat/Mouse Growth Hormone ELISA kit from Millipore® (Cat. #EZRMGH-45K). Samples were diluted 10-fold with the assay buffer and 10 µl of the diluted samples were added along with 90 µl of assay buffer to the ELISA plate. The remainder of the assay was performed according to the manufacturer's protocol.

Reporter Gene Assay.

BHK cells stably transfected with the human GRF receptor and an alkaline phosphatase reporter gene were plated in 96-well plates at $5 \times 10^4$ cells/well and incubated overnight. The next day, cells were washed twice with PBS and maintained for 10-30 min. in assay buffer (DMEM without phenol red, 20 mM HEPES and 1% heat-inactivated fetal bovine serum (FBS)). Peptides from $10^{-5}$ M to $10^{-12}$ M were added to the cells and incubated for 24 h. The alkaline phosphatase level in the culture supernatants were performed using the Alkaline Phosphatase detection kit from Invitrogen® (cat. #T1017).

Statistical Analysis.

The standard curve was plotted using the 4-parameter logistic equation using GraphPad Prism™ software and was used to determine the GH concentration of plasma samples. The data were analyzed using one-way analysis of variance. Bonferroni's test was used to make comparisons among different treatments.

GH Response in Rats.

Figure 2:
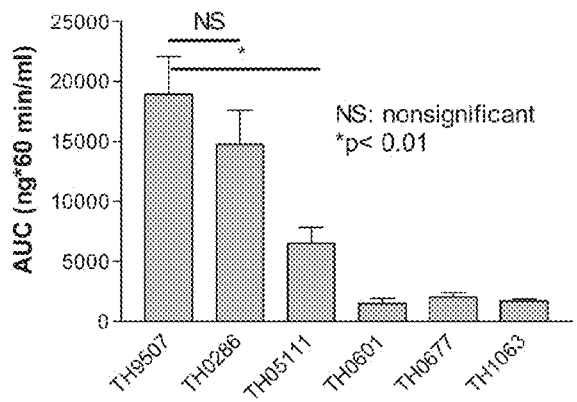
FIG. 2 shows the $AUC_{(0-60\ min)}$ of GH elicited by TH9507 impurities (as defined below; TH1063: see Table 1) in female rats.
Figure 3:
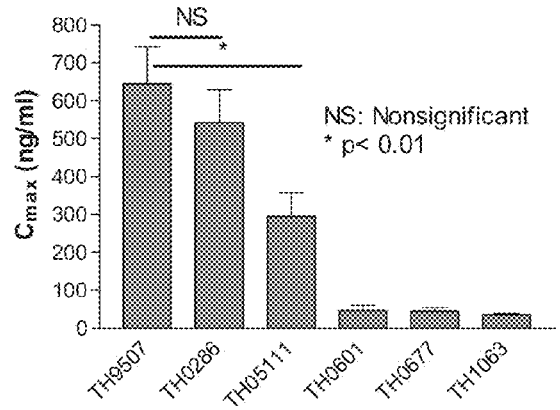
FIG. 3 shows the $C_{max}$ of GH produced by TH9507 impurities (as defined below) in female rats.

Results are shown in Table 1 and FIGS. 1-3. The TH9507 impurities TH0677 and TH1063 did not stimulate GH secretion in rats. However, TH0286, TH05111 and TH0601 elicited GH secretion with AUCs of 1.3, 2.9 and 12.4 fold and $C_{max}$ of 1.2, 2.2 and 14.0 fold lower than TH9507 respectively. AUC and $C_{max}$ between TH9507 and TH0286 were not significantly different.

TABLE 1

Summary of $AUC_{(0-60min)}$ and $C_{max}$ of GH responses to TH9507 impurities

| Product Code | Product Name | Chemical Sequence | Formulation | AUC (ng * min/ml) | $C_{MAX}$ (ng/ml) | $T_{MAX}$(min) | n (rats) |
|---|---|---|---|---|---|---|---|
| TH9507 | Tesamorelin | Hexenoyl-Y-A-D-A-I-F-T-N-S-Y-R-K-V-L-G-Q-L-S-A-R-K-L-L-Q-D-I-M-S-R-Q-Q-G-E-S-N-Q-E-R-G-A-R-A-R-L-NH2 | 5% mannitol | 18953 ± 6317 | 645 ± 194 | 10 | 4 |
| TH0286 | N-Hex-hGRF[1-44]Met[O]27 amide | Trans-3-hexenoyl-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met[O]-Ser-Arg-Gln-Gln-Gly-Glu-Ser-Asn-Gln-Glu-Arg-Gly-Ala-Arg-Ala-Arg-Leu-NH2 | 5% mannitol | 14751 ± 5745 | 542 ± 173 | 10 | 4 |
| TH05111 | TH9507 Asp8 | Hexenoyl-Y-A-D-A-I-F-T-D-S-Y-R-K-V-L-G-Q-L-S-A-R-K-L-L-Q-D-I-M-S-R-Q-Q-G-E-S-N-Q-E-R-G-A-R-A-R-L-NH2 | 5% mannitol | 6540 ± 2647 | 294 ± 126 | 5 | 4 |
| TH0601 | TH9507 beta-Asp8 | Hexenoyl-Y-A-D-A-I-F-T-beta D-S-Y-R-K-V-L-G-Q-L-S-A-R-K-L-L-Q-D-I-M-S-R-Q-Q-G-E-S-N-Q-E-R-G-A-R-A-R-L-NH2 | 5% mannitol | 1533 ± 734 | 46 ± 30 | 5 | 4 |
| TH0677 | TH9507 beta-Asp3 | trans-3-Hexenoyl-Y-A-beta D-A-I-F-T-N-S-Y-R-K-V-L-G-Q-L-S-A-R-K-L-L-Q-D-I-M-S-R-Q- | 5% mannitol | NR | NR | NR | 4 |

TABLE 1-continued

Summary of AUC$_{(0-60min)}$ and C$_{max}$ of GH responses to TH9507 impurities

| Product Code | Product Name | Chemical Sequence | Formulation | AUC (ng * min/ml) | C$_{MAX}$ (ng/ml) | T$_{MAX}$(min) | n (rats) |
|---|---|---|---|---|---|---|---|
| TH1063 | TH9507 cyclic form at Asp$^3$ | Q-G-E-S-N-Q-E-R-G-A-R-A-R-L-NH2 trans-3-Hexenoyl-Y-A-X-A-I-F-T-N-S-Y-R-K-V-L-G-Q-L-S-A-R-K-L-L-Q-D-I-M-S-R-Q-Q-G-E-S-N-Q-E-R-G-A-R-A-R-L-NH2 (for X see below) | 5% mannitol | NR | NR | NR | 4 |

NR: no response

X = 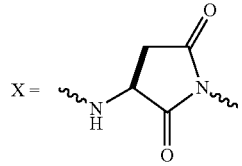

The products of degradation/isomerization at Asp$^3$ and Asp$^8$ in β-configuration, i.e. TH0601 and TH0677, are shown to be biologically inactive species. Therefore, their level in pharmaceutical formulations of tesamorelin should be kept at a minimal possible level.

The amino acid sequence of tesamorelin corresponds to that of naturally occurring Growth Hormone Releasing Peptide (GRF). GRF belongs to the glucagon/secretin family of peptide hormones that share primary structure similarities. Among all the peptide hormones in the glucagon/secretin family, only GRF has an Asn residue at position 8; other biomolecules contain either Asp or Ser residues. Of note, the analog of tesamorelin bearing Asp$^8$ in an α-configuration, i.e. TH05111, has been reported to be equipotent in vitro and retains ~30% of GH-releasing activity in vivo compared to parent molecule (FIG. 1).

In Vitro Potency and Efficacy.

Figure 4:
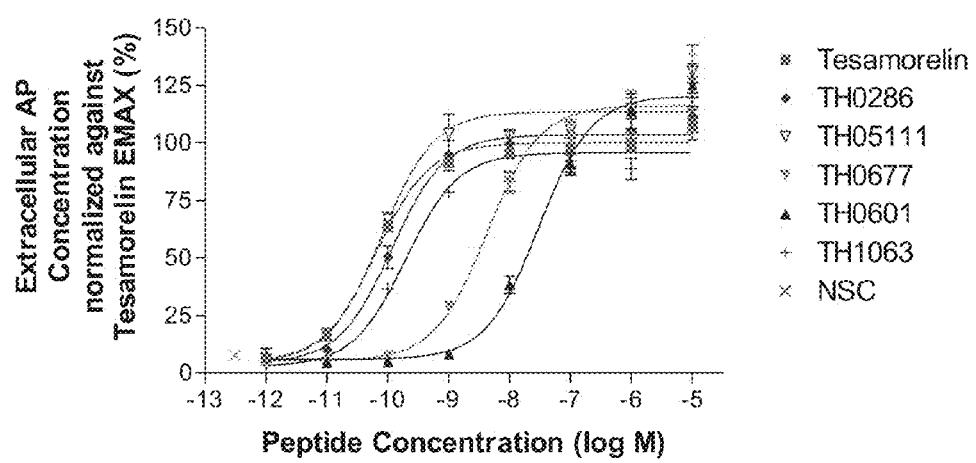
FIG. 4 shows the dose-responses of TH9507 impurities (as defined below) in a cell-based assay.

Results are shown in Table 2 and FIG. 4. All impurities produced reporter gene expression but not with the same potencies. TH0286, TH05111 and TH1063 EC$_{50}$s are comparable to TH9507. However, β-Asp peptides (TH0601 and TH0677) were less potent with EC$_{50}$ s 500- and 71-fold higher than TH9507 respectively.

TABLE 2

Dose-response parameters of TH9507 impurities

| Peptides | Product Name | Sequence | EC50 (nM) | EMAX (%) | SNR | n (experiments) |
|---|---|---|---|---|---|---|
| TH9507 | Tesamorelin | Hexenoyl-Y-A-D-A-I-F-T-N-S-Y-R-K-V-L-G-Q-L-S-A-R-K-L-L-Q-D-I-M-S-R-Q-Q-G-E-S-N-Q-E-R-G-A-R-A-R-L-NH2 | 0.06 ± 0.02 | 100.0 ±11.3 | 22.3 | 3 |
| TH0286 | N-Hex-hGRF[1-44] Met[O]27 amide | Trans-3-hexenoyl-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met[O]-Ser-Arg-Gln-Gln-Gly-Glu-Ser-Asn-Gln-Glu-Arg-Gly-Ala-Arg-Ala-Arg-Leu-NH2 | 0.16 ± 0.03 | 103.5 ± 21.6 | 23.1 | 3 |
| TH05111 | TH9507 Asp 8 | Hexenoyl-Y-A-D-A-I-F-T-D-S-Y-R-K-V-L-G-Q-L-S-A-R-K-L-L-Q-D-I-M-S-R-Q-Q-G-E-S-N-Q-E-R-G-A-R-A-R-L-NH2 | 0.08 ± 0.02 | 113.6 ± 17.0 | 25.3 | 3 |
| TH0601 | TH9507 beta-Asp 8 | Hexenoyl-Y-A-D-A-I-F-T-beta D-S-Y-R-K-V-L-G-Q-L-S-A-R-K-L-L-Q-D-I-M-S-R-Q-Q-G-E-S-N-Q-E-R-G-A-R-A-R-L-NH2 | 30.0 ± 30.4 | 120.5 ± 23.5 | 26.9 | 3 |
| TH0677 | TH9507 beta-Asp3 | trans-3-Hexenoyl-Y-A-beta D-A-I-F-T-N-S-Y-R-K-V-L-G-Q-L-S-A-R-K-L-L-Q-D-I-M-S-R-Q-Q-G-E-S-N-Q-E-R-G-A-R-A-R-L-NH2 | 4.24 ± 1.45 | 116.2 ± 25.8 | 25.9 | 3 |
| TH1063 | GRF | trans-3-Hexenoyl-Y-A-X-A-I-F-T-N-S-Y-R-K-V-L-G-Q-L-S-A-R-K-L-L-Q-D-I-M-S-R-Q-Q-G-E-S-N-Q-E-R-G-A-R-A-R-L-NH2 (for X see Table 1) | 0.20 ± 0.07 | 95.7 ± 8.1 | 21.3 | 2 |

SNR: signal to noise ratio

In summary, all the TH9507 impurities were active in vitro. TH0286, TH05111 and TH1063 potencies were comparable to TH9507. TH0601 and TH0677 were less potent. TH0286, TH05111 and TH0601 stimulated GH secretion with different potencies, all of which were less than that of TH9507; the differences between TH9507 and TH0286 were not significant.

Example 3

Formulations

Various formulations comprising tesamorelin (see Table 3, below) were prepared and were stressed under accelerated stability conditions, e.g. 25° C., 37° C., and 45° C., and the degradation of the tesamorelin under stress conditions was then analyzed and compared to that of control. The formulation containing from 4 to 8 mg/mL of tesamorelin in the presence of 4% mannitol and 2% sucrose or 5% mannitol were used as a control.

TABLE 3

Formulations prepared and tested under accelerated conditions

| Formulation # | TH9507 Concentration | pH | pH modifier | Excipient | Antimicrobial Agent |
|---|---|---|---|---|---|
| LF1 | 6 mg/ml | 5.5 | N/A | 5% Mannitol | 0.9% benzyl alcohol |
| LF2 | 6 mg/ml | 3.0 | Lactic acid | 5% Mannitol | 0.9% benzyl alcohol |
| LF3 | 6 mg/ml | 3.0 | Acetic Acid | 5% Mannitol | 0.9% benzyl alcohol |
| LF4 | 6 mg/ml | 3.0 | Lactic acid | $MgCl_2$ 50 mM; 7% sucrose | 0.9% benzyl alcohol |
| LF5 | 1 mg/ml | 5.5 | N/A | 9% Sucrose | N/A |
| LF6 | 6 mg/ml | 4.0 | 0.03M Lactic acid | 5% Mannitol | 0.9% benzyl alcohol |
| LF7 | 6 mg/ml | 4.0 | 0.03M Glutamic acid | 5% Mannitol | 0.9% benzyl alcohol |
| LF8 | 6 mg/ml | 4.0 | 0.03M Aspartic acid | 5% Mannitol | 0.9% benzyl alcohol |
| LF9 | 6 mg/ml | 4.8 | 0.03M Glycine | 5% Mannitol | 0.9% benzyl alcohol |
| LF10 | 6 mg/ml | 4.0 | Sodium chloride/HCl | 5% Mannitol | 0.9% benzyl alcohol |
| LF11 | 6 mg/ml | 3.0 | Lactic acid | Zn Acetate | 0.9% benzyl alcohol |
| LF12 | 6 mg/ml | 4.0 | Lactic acid | Zn Acetate | 0.9% benzyl alcohol |
| LF13 | 6 mg/ml | 3.0 | Lactic acid | Mg Acetate | 0.9% benzyl alcohol |
| LF14 | 6 mg/ml | 4.0 | Lactic acid | Mg Acetate | 0.9% benzyl alcohol |
| LF15 | 6 mg/ml | 5.0 | N/A | 5% Mannitol | 0.9% benzyl alcohol |
| LF16 | 6 mg/ml | 6.0 | N/A | 5% Mannitol | 0.9% benzyl alcohol |
| LF17 | 6 mg/ml | 3.0 | N-Acetylcysteine | 5% Mannitol | 0.9% benzyl alcohol |
| LF18 | 8 mg/mL | 5.0 | N/A | 2.5% Glycine | 0.9% benzyl alcohol |
| LF19 | 8 mg/mL | 5.0 | N/A | 2.5% Glycine | 0.3% m-cresol |
| LF20 | 8 mg/mL | 5.0 | N/A | 2.5% Glycine; 0.05% methionine | 0.3% m-cresol |
| LF21 | 8 mg/mL | 4.5 | 0.025M lactate Na | 10% HP-β-Cyclodextrin | 0.3% m-cresol |
| LF22 | 8 mg/mL | 4.5 | 0.025M lactate Na | 5% HP-β-Cyclodextrin; 2.5% Mannitol | 0.3% m-cresol |
| LF23 | 8 mg/mL | 4.5 | 0.025M lactate Na | 2% HP-β-Cyclodextrin; 4% Mannitol | 0.3% m-cresol |
| LF24 | 8 mg/mL | 4.5 | 0.025M lactate Na | 5% Mannitol | 0.3% m-cresol |
| LF25 | 8 mg/mL | 5.0 | N/A | 5% Mannitol | 0.3% m-cresol |
| LF26 | 8 mg/mL | 5.5 | N/A | 5% Mannitol | 0.3% m-cresol |
| LF27 | 6 mg/mL | 5.5 | N/A | 5% Mannitol | 0.3% m-cresol |
| LF28 | 8 mg/mL | 6.0 | 0.01 Lactate Na | 5% Mannitol | 0.3% m-cresol |
| LF29 | 8 mg/mL | 6.0 | 0.01 Lactate Na | 2% HP-β-Cyclodextrin; 4% Mannitol | 0.3% m-cresol |
| LF30 | 8 mg/mL | 6.0 | 0.01 Lactate Na | 5% HP-β-Cyclodextrin; 2.5% Mannitol | 0.3% m-cresol |
| LF31 | 8 mg/mL | 6.0 | 0.01 Lactate Na | 10% HP-β-Cyclodextrin | 0.3% m-cresol |

The concentrations of the bulking excipients, i.e. mannitol, sucrose etc., were close or corresponded to the isotonic concentration. In various formulations, benzyl alcohol or m-cresol was chosen as an antimicrobial preservative. It was observed during HPLC analysis that apart from typical degradants, i.e. β-$Asp^8$-(TH0601), $Asp^8$-(TH05111), β-$Asp^3$-(TH0677), $Asu^3$-(TH1063), and $Met^{27}$ (Ox)-tesamorelin (TH0286), unknown impurities having RRT of 0.78 and 0.83-0.85 were formed in the formulations.

Example 4

Effect of Tesamorelin Concentration and pH

Figure 5:
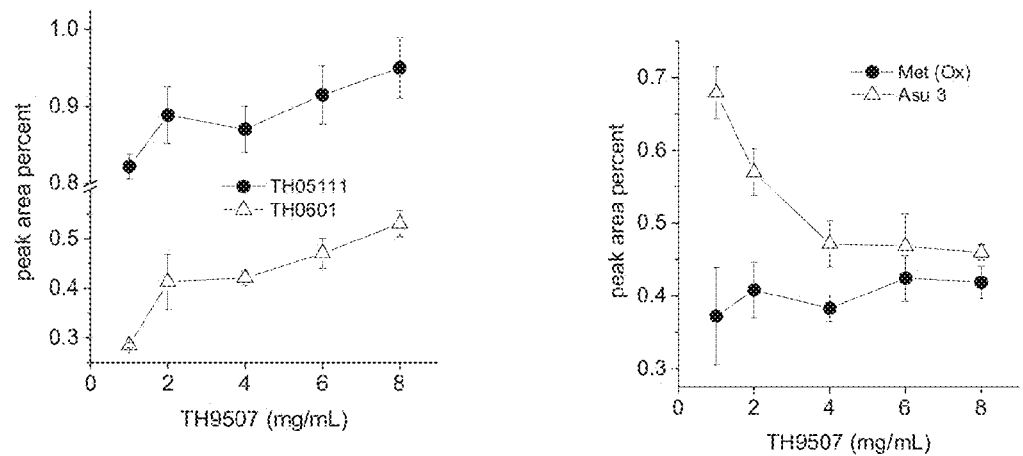
FIG. 5 shows the effect of tesamorelin concentration on the level of the degradants after incubation in a solution of 4% mannitol and 2% sucrose, pH 5.5, at 25° C. for 10 days (TH0511: $Asp^8$ tesamorelin; TH0601: $\beta$-$Asp^8$ tesamorelin; Met (Ox): $Met^{27}$-oxidized tesamorelin; $Asu^3$: tesamorelin with succinimidyl intermediate in the transformation of $Asp^3$ into the $\beta$-$Asp^3$ derivative)

The level of various degradation products was assessed in formulations containing 4% mannitol and 2% sucrose and different concentrations of tesamorelin at pH5.5. As seen in FIG. 5, an increased susceptibility of $Asn^8$ to deamidation was observed in more concentrated tesamorelin solutions (4-8 mg/mL). $Asp^3$ residues were found to be less susceptible to degradation in the 4-8 mg/mL tesamorelin solutions compared to less concentrated solutions, and no effect of tesamorelin concentration was found on the oxidation rate of $Met^{27}$.

Figure 6:
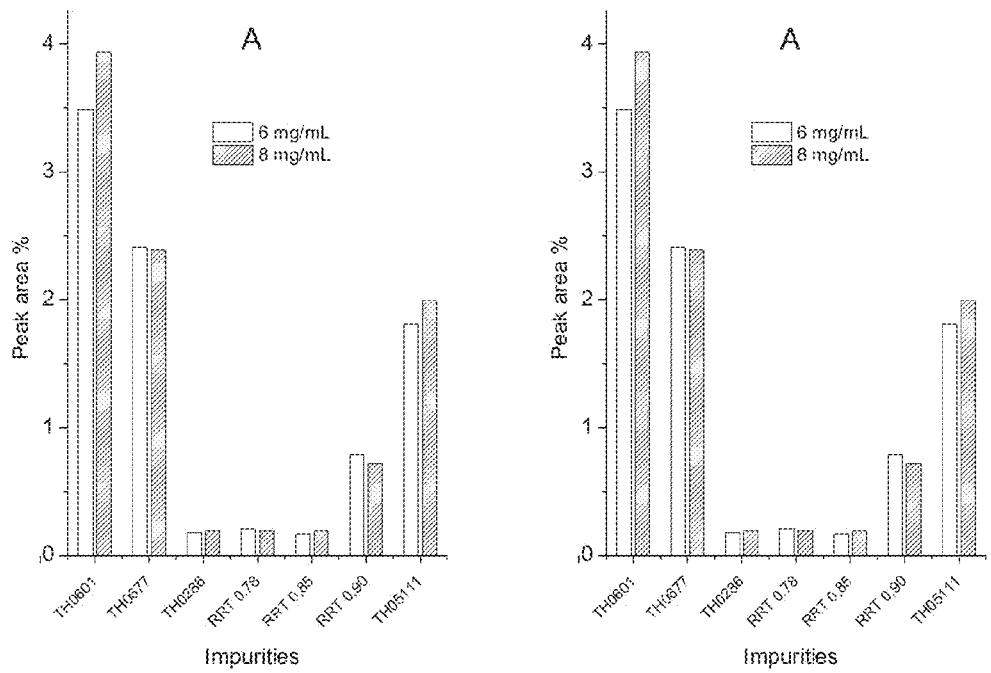
FIG. 6 shows the content of the major degradants after 4 days of incubation at 45° C. (A) and 8 days at 37° C. (B) in liquid formulations containing 6 mg/mL and 8 mg/mL of tesamorelin (TH0601, TH0511 and RRT0.90: as defined above; TH0677: $\beta$-$Asp^3$ tesamorelin; TH0286: $Met^{27}$-oxidized tesamorelin; RRT 0.78 and RRT 0.85 are unknown impurities)

In further studies, the content of impurities in formulations containing 6 mg/mL and 8 mg/mL of tesamorelin at pH5.5 (both contain 0.3% m-cresol) after incubation at 45° C. and 37° C. was compared as shown in FIG. 6. As can be seen from these data, only the content of TH0601 was found to be significantly affected by the tesamorelin concentration. In general, the stability potential of 6 mg/mL and 8 mg/mL formulations at pH 5.5 can be considered comparable, and as such the effect of pH was studied using 6- and 8-mg/mL tesamorelin formulations.

Figure 7:
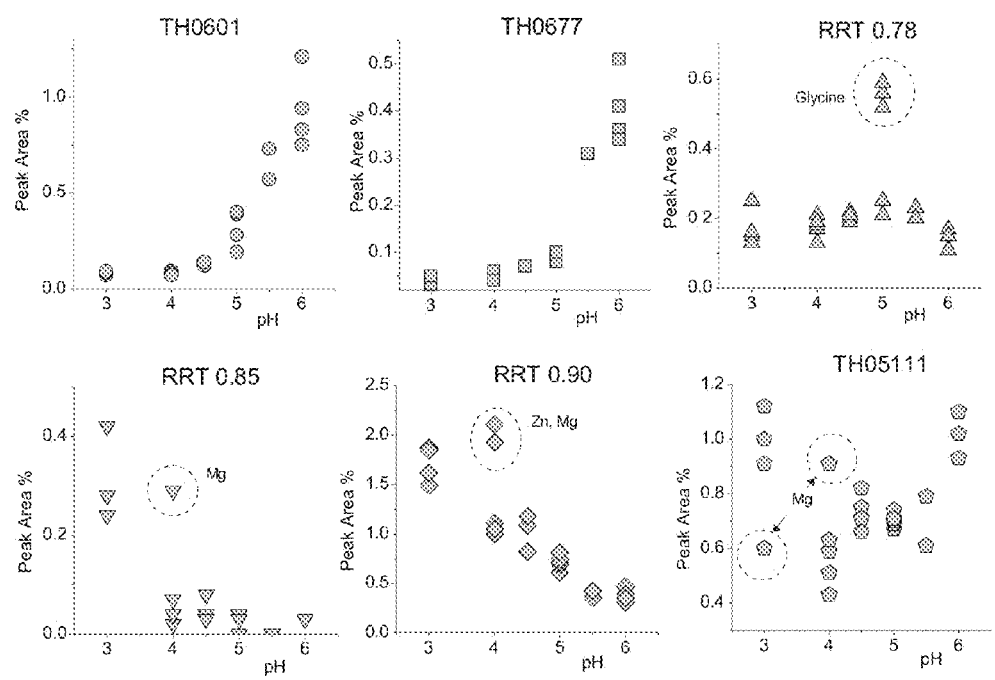
FIG. 7 shows the content the major degradation products as a function of pH in the liquid formulation of tesamorelin (6-8 mg/mL) after incubation at 25° C. for 12 days (TH0601, TH0677, TH0511, RRT 0.78, RRT 0.85 and RRT0.90: as defined above)

In order to further examine the effect of pH on degradation, the content of impurities in the tested formulations (Table 1) was plotted as a function of pH. As can be seen in FIG. 7, weakly acidic conditions (pH<5) favour formation of succinimide (RRT 0.90 (TH1063) impurity) and the RRT 0.85 impurity, while acidic and close-to-neutral pHs (pH3 and pH>5) stimulate deamidation at $Asn^8$, generating higher content of β-$Asp^8$-(TH0601) and α-$Asp^8$-(TH05111) derivatives.

It can also be observed that addition of Glycine as a tonicity agent promotes formation of the RRT 0.78 impurity at pH5 (FIG. 7). When mannitol or HP-β-CD is used as a tonicity agent (5%), appearance of RRT 0.78 is rather pH-independent. Formation of the α-$Asp^8$-derivative (TH05111) as well as RTT 0.85 and RRT 0.90 impurities at pH4 is apparently catalyzed by $Mg^{2+}$ and $Zn^{2+}$ ions (FIG. 7). At the same time, $Mg^{2+}$ shows inhibitory effect on TH05111 formation at pH3.

Of note, the content of the RRT0.90 impurities decreases linearly with increasing pH. At the same time both deamidation (TH0601) and isomerization (TH0677) products shows exponential increase as pH increases from pH4 to pH6 (FIG. 5).

Example 5

Effect of Hydroxypropyl-Betadex Addition

Figure 8:
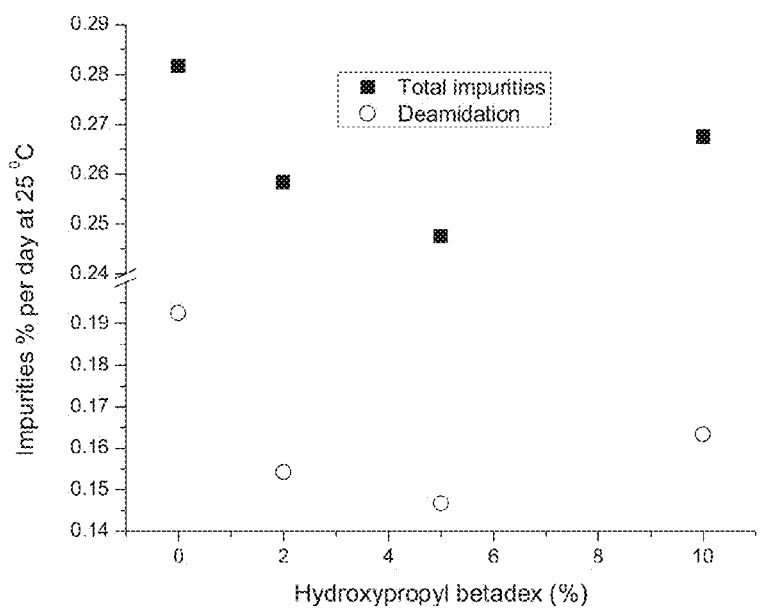
FIG. 8 shows the effect of hydroxypropyl betadex on the degradation of tesamorelin in solution at pH 6.0.

It was surprisingly found that addition of hydroxypropyl-beta-cyclodextrin, HP-β-CD or hydroxypropyl betadex, at 2-10% (w/v), improves chemical stability of tesamorelin, and particularly resistance to deamidation, compared to other formulations (FIG. 8).

Cyclodextrins are believed to be useful in solubilizing poorly soluble peptides in liquid formulations. However, the stabilizing effect of cyclodextrin against deamidation and isomerization of the $Asn^8$ residue cannot be explained by direct interactions of $Asn^8$ with hydroxypropyl betadex as was shown by NMR (see below).

The effect of HP-β-CD concentration on the rate of tesamorelin degradation was further studied by varying the content of HP-β-CD in the presence of different amounts of mannitol in order to keep the solutions isotonic. Given that the solution containing either 5% mannitol or 25% HP-β-CD are isotonic, the combinations of mannitol and HP-β-CD were prepared in the following proportions:

0% HP-β-CD with 5% mannitol;
2.5% HP-β-CD with 4.7% mannitol;
5% HP-β-CD with 4.3% mannitol;
10% HP-β-CD with 3.5% mannitol;
25% HP-β-CD with 0% mannitol;

All the solutions were prepared in 0.01M sodium lactate and pH was adjusted to pH6.

Analytical Methods.

Purity, content of parent compound and individual impurities, was tested by HPLC on a reversed-phase column using the gradient of acetonitrile in aqueous 0.1% trifluorocetate solution to resolve the parent compound and related substances. The formulation solutions were diluted to contain 1 mg/mL of tesamorelin acetate.

For the NMR measurements, the samples were spiked with $D_2O$ at 10%. The 1H NMR spectra were acquired on a Varian INOVA at 600 MHz. Pulse sequences with water pre-saturation (Biopack, Varian) were used for the 1D and 2D-correlated spectroscopy (COSY), nuclear Overhauser effect spectroscopy (NOESY) and homonuclear Hartmann-Hahn (HOHAHA or TOCSY). The FIDs have been Fourier-Transformed with the VNMR software (Varian) using standard apodization procedures. Spectra were plotted to files in pdf format using CCPNMR and converted to PNG subsequently.

The Circular Dichroism (CD) spectra were recorded using a Jasco-810 spectropolarimeter. The CD spectra were recorded from 300 nm to 190 nm at 20° C. and at 37° C. The samples of tesamorelin formulations were prepared with the peptide concentration of 1 mg/mL. Tesamorelin was dissolved in the solutions containing 0%, 1%, 2.5%, 5%, 10%, and 15% of HP-β-CD.

Results.

The stabilizing effect of HP-β-CD with the respect to deamidation at $Asn^8$ was unexpected in view of the purely physical nature of the interactions between two compounds. The existence of physical interactions between N-terminal portion of tesamorelin molecule and HP-β-CD was confirmed by UV spectroscopy and NMR.

UV Spectroscopy.

Figure 9A:
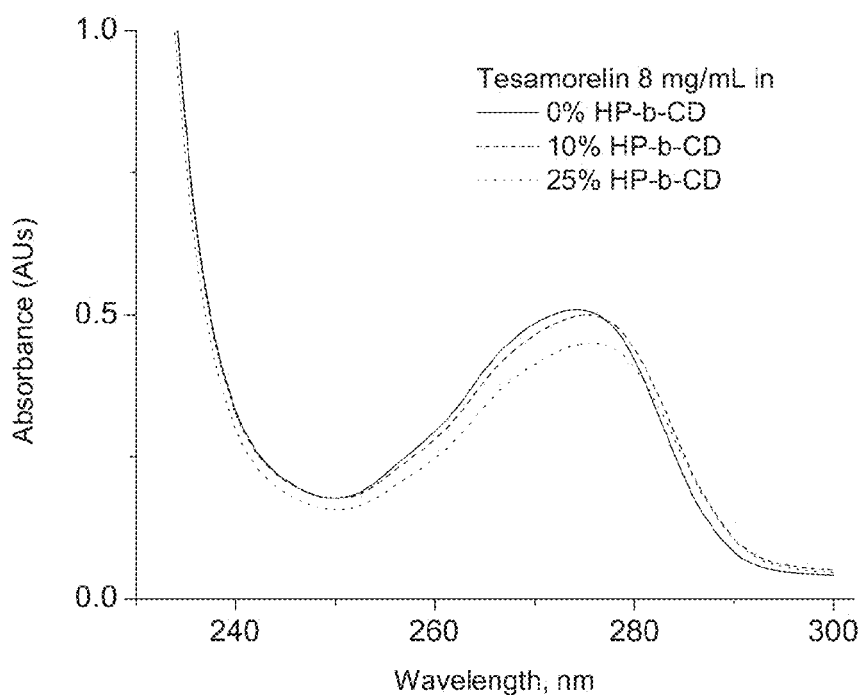
FIG. 9A shows the UV spectra of tesamorelin (8 mg/mL) in the presence of HP-$\beta$-CD. The changes induced by HP-$\beta$-CD concerns mainly absorbance by aromatic residues (250-290 nm). The spectra are recorded at 2 nm resolution in a 1 mm quartz cuvette.

In order to verify whether hydrophobic residues interact with HP-β-CD the UV spectra of tesamorelin were recorded and analyzed in the presence of different concentration of HP-β-CD. Typical UV spectra of tesamorelin in the presence of different amount of HP-β-CD are shown in FIG. 9A. The spectrum of tesamorelin in water features a broad band with a maximum at 276 nm as a result of the overlap of adsorption bands of Phe and Tyr (Svane A. S. P. et al., 2008, *Biophys J.*, 95: 366-377; Balestrieri C. et al., 1978, *Eur. J. Biochem.* 90: 433-440). Addition of HP-β-CD induces a shift to longer wavelengths and a decrease in the intensity of the 276-nm band (FIG. 9A).

Figure 9B:
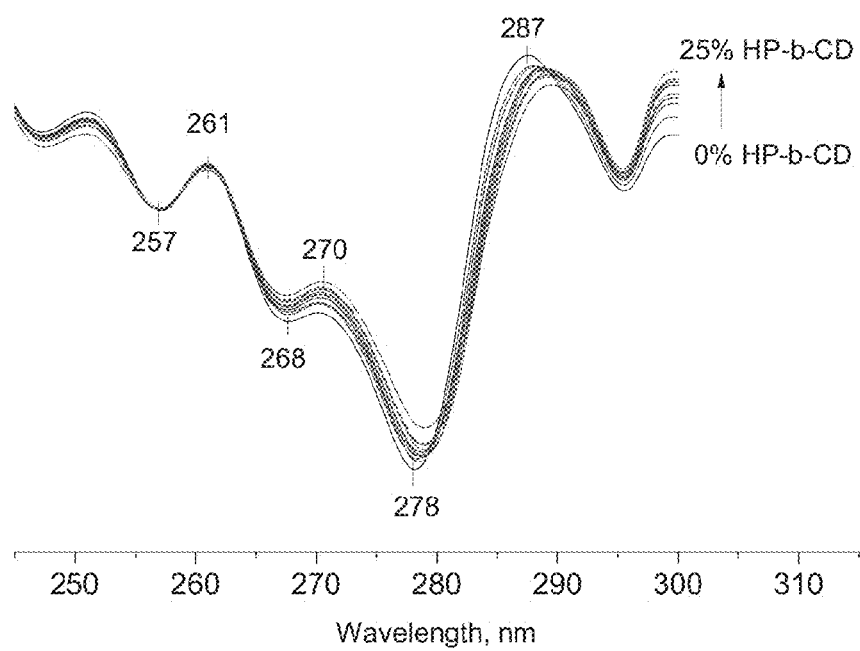
FIG. 9B shows second-derivative spectra of tesamorelin (8 mg/mL) in the presence of different concentrations of HP-$\beta$-CD (from 0% to 25% (w/v), with 2.5% increments)

Second-derivative UV spectra of tesamorelin in the presence of different concentrations of HP-β-CD were then analyzed in order to detect changes in the absorption by Phe versus Tyr residues. The broad band in the 250-280 region shows a number of components centered at 257, 261, 267, 270 and 278 nm in the second-derivative spectra (FIG. 9B). Since Phe is known to absorb UV at shorter wavelength, the signals at 261 (positive maxima) is attributed to this aromatic residue. The component at 278 nm (negative maxima) is assigned to the Tyr absorption band. The location and relative intensity of the components in the second-derivative spectra correspond well to those reported for Phe and Tyr residues (Svane A. S. P. et al., supra; Balestrieri C. et al., supra).

A noticeable shift is observed for the maxima of the Tyr component in the second-derivative spectra, i.e. the signal is centered at 278 nm in 0% HP-β-CD and shifts to 279 nm in 25% HP-β-CD solution (FIG. 10). This indicates that HP-β-CD interacts with the aromatic moiety of at least Tyr residues in tesamorelin.

To better visualize the changes in the shape and intensities of the Phe and Tyr components in second-derivative spectra, the differential second-derivative spectra of tesamorelin in the presence of HP-β-CD were analyzed. The differential second-derivative spectra were obtained by subtracting the spectrum registered in water from those recorded in the HP-β-CD solution (FIG. 11).

The changes in the location and intensity of the Tyr signal in the presence of HP-β-CD leads to appearance of positive signal at 276 nm and a negative signal at 284 nm (FIG. 11). The intensity of both 276 nm and 284 nm signals change with increasing HP-β-CD concentration, while the intensity of the band at 261 nm due to Phe absorption is unaffected by HP-β-CD (FIG. 11).

These findings suggest that the UV spectra of Tyr residues show a shift to the longer wavelength, whereas UV spectra of Phe present no changes in the position and intensity of the absorption band.

The results of UV spectra analysis showed that HP-β-CD interacts predominantly with the N-terminus of the peptide portion of tesamorelin, more specifically with residue Tyr1 and not with a region close to the Phe 6 residue.

NMR.

Figure 12:
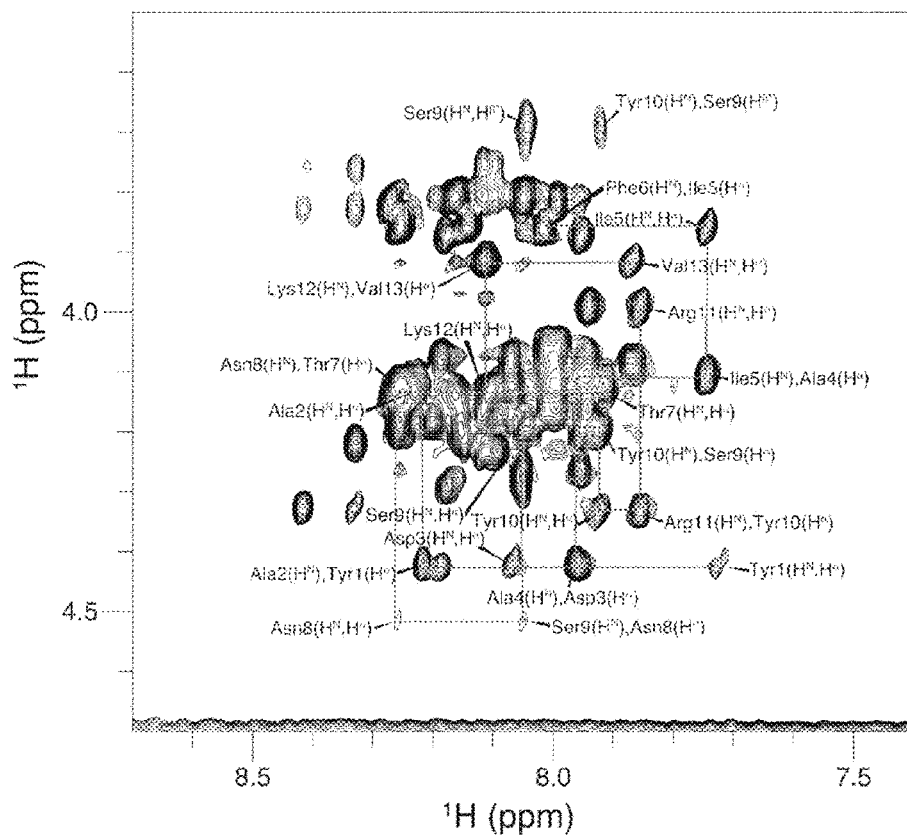
FIG. 12 shows the fingerprint region of the $^1H,^1H$-NOESY spectrum of unlabelled tesamorelin. Sequential $d_{\alpha,N}(i,i+1)$ for residues 1 to 13 are labelled.

Nuclear Magnetic Resonance (NMR) was used to characterize the N-terminal region of tesamorelin in aqueous solution and its interaction with HP-β-CD. The NMR spectra obtained in absence of HP-β-CD allowed the specific attribution of residues Tyr1 to Val13 of tesamorelin. Briefly, the specific assignment of the isotopically labelled residues was done by identification of the specific spin systems in the multidimensional experiments. After specific assignment of isotopically labelled residues was completed, the $^1H$-$^1H$ NOESY and the $^{15}N$-edited NOESY spectra were used to identify the spin systems of adjacent residues to allow for their complete assignment using the $^1H$-$^1H$ TOCSY and COSY spectra. As shown by the NOESY spectrum fingerprint region displayed in FIG. 12, the specific and sequential assignment was successfully carried out for residues Tyr1 to Val13.

Figure 13:
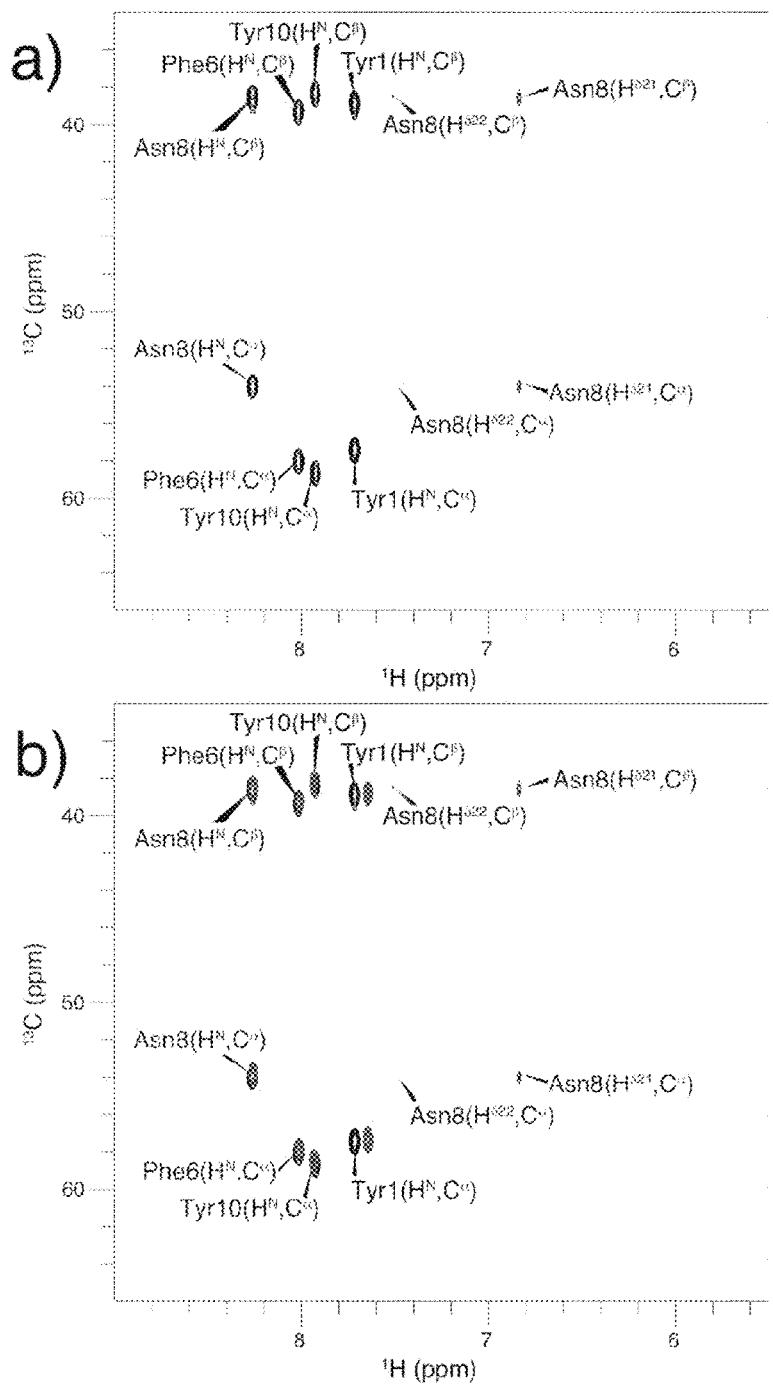
FIG. 13 shows HNCACB spectra of isotopically labelled residues of tesamorelin (a) in absence and (b) in presence of HP-$\beta$-CD (gray overlay)
Figure 14:
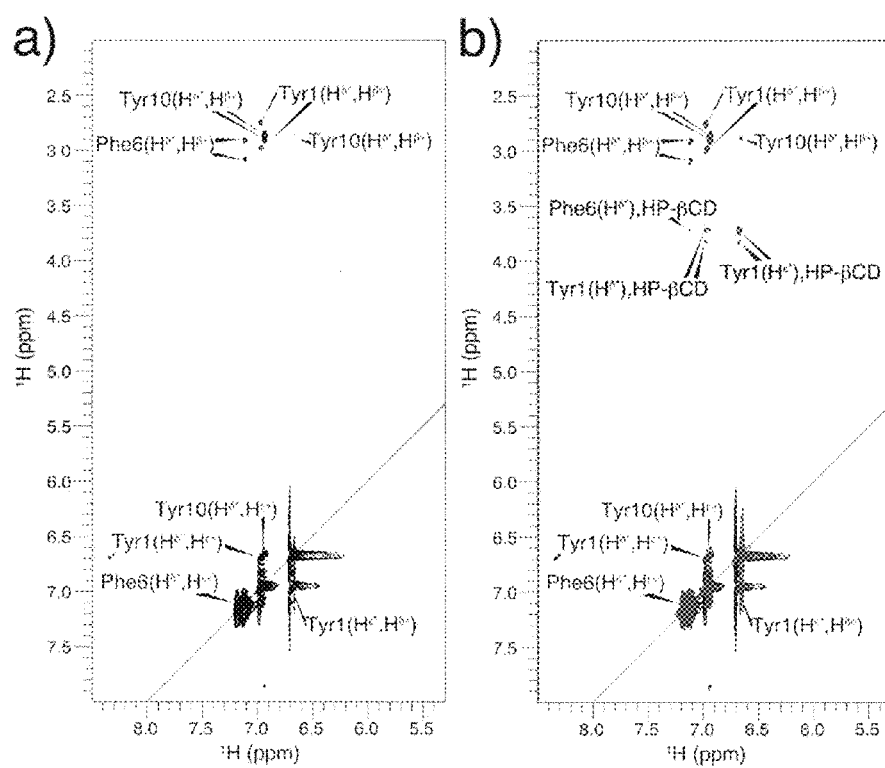
FIG. 14 shows the F1, F3 plane of the $^{13}C$-edited NOESY spectrum (aromatic region) of tesamorelin (a) in absence and (b) in presence of HP-$\beta$-CD (gray overlay)

Comparison of the multidimensional NMR spectra in absence and in presence of HP-β-CD enabled identification of the interactions with tesamorelin (FIGS. 13 and 14). Indeed, as can be seen on the spectra, the chemical shifts of the labelled residues is generally unaffected by the presence of HP-β-CD, with the notable exception of Tyr1 crosspeaks, that display clear chemical shift variations in all the experiments recorded in presence of HP-β-CD (FIG. 13). Moreover, the presence of additional cross-peaks in the aromatic region of the $^{13}$C-edited NOESY spectrum (FIG. 14) reveals a direct interaction between HP-β-CD and residues Tyr1 and Phe6 of tesamorelin, more precisely the Hδ* and Hε* atoms of these residues. Note that the stronger intensity of NOEs for Tyr1 suggests a preferential interaction of HP-β-CD with that residue. No direct interactions between Asn$^8$ and HP-β-CD were detected.

Effect of Hydroxypropyl-Betadex on Tesamorelin Conformation.

Figure 15:
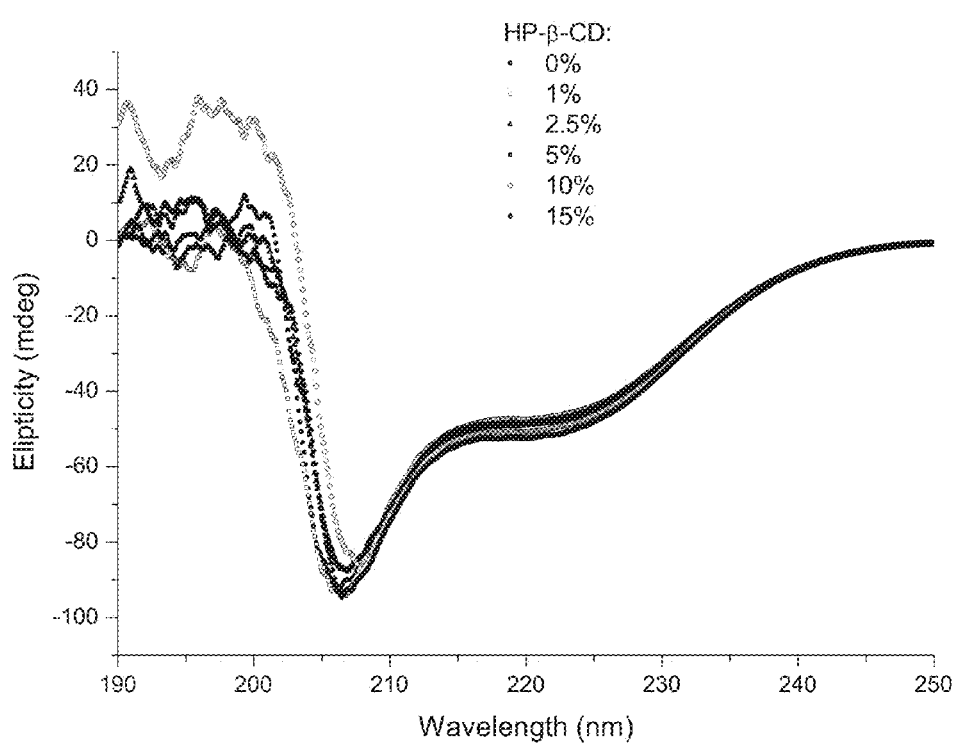
FIG. 15 shows circular dichroism spectra (average of 3 scans) of tesamorelin in the presence HP-$\beta$-CD in solution. The concentration of tesamorelin is 1 mg/mL. The spectra were recorded at 20° C.

In order to verify if addition of HP-β-CD to a tesamorelin solution induces significant conformational changes, the CD spectra of tesamorelin in the presence of HP-β-CD were recorded and analyzed (FIG. 15). The UV CD spectra within the 170-250 nm interval are dominated by the contribution of the peptide bonds because of the predominance of peptide bonds relative to other chromophores in the peptide structure. Therefore, a far UV-CD spectrum reflects the ensemble of the specific dihedral angles of polypeptide chain, and is characteristic for certain average biomolecule's conformation (Baudyš M., et al., "Peptide and Protein Characterization" in *Pharmaceutical formulation Development of Peptides and Proteins*, Frokjaer S., Hovgaard L. (Eds.). Taylor & Francis, 2000).

The CD spectra of tesamorelin in solutions are characteristic of random conformation with some minor contribution of α-helical structures, as it follows from the weak ellipticity at 222 nm (FIG. 15). The intensity of the CD signal at 205 nm and 222 nm is preserved in the presence of HP-β-CD, which indicates that the addition of this excipient does not induce major conformational changes of tesamorelin.

Effect of Hydroxypropyl Betadex Concentration.

Following identification of HP-β-CD as a formulation component that improves the stability of tesamorelin in solution against deamidation at pharmaceutically acceptable pH, the effect of HP-β-CD concentration on the chemical stability of the peptide was investigated.

Figure 16:
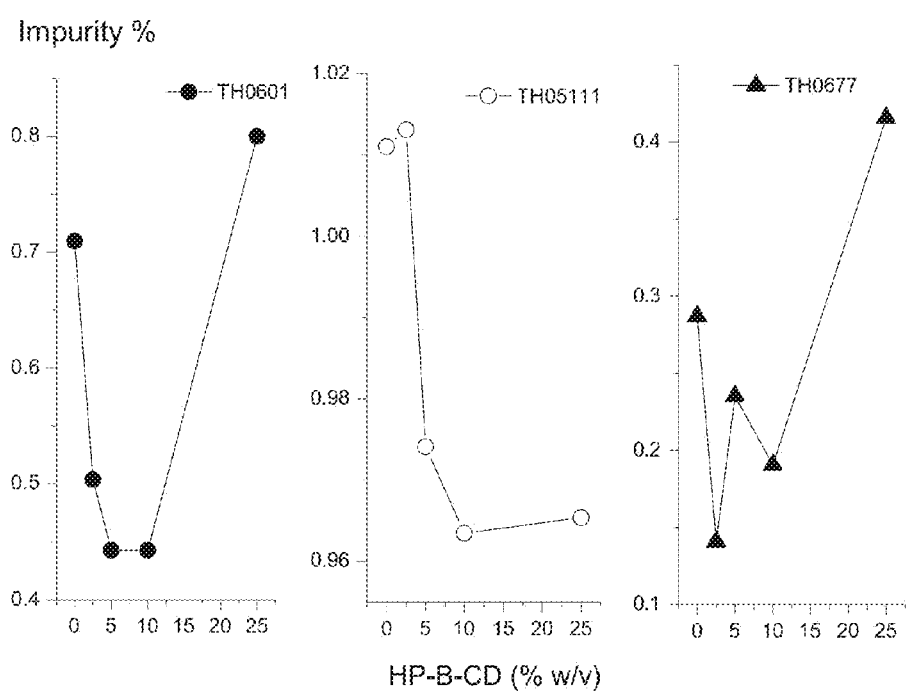
FIG. 16 shows the effect of HP-$\beta$-CD concentration on the formation of deamidated tesamorelin degradants. The formulations containing 8 mg/mL of tesamorelin and different concentrations of HP-$\beta$-CD were incubated at 15° C. for 14 days.

The results of the accelerated stability study of the formulation containing 8 mg/mL of tesamorelin and different concentration of HP-β-CD is shown in FIG. 16. As can be seen in FIG. 16, HP-β-CD has a profound effect on the stability potential of tesamorelin in solution. Degradation through deamidation (TH0601, TH05111) and isomerization of the Asp residue (TH0677) is substantially repressed in the solutions containing 5%-10% HP-β-CD compared to HP-β-CD-free formulation. However, the stabilizing effect with respect to the formation of TH0601 and TH0677 is no longer present when the concentration of HP-β-CD reaches 25% (FIG. 16).

On the basis of the results obtained (FIG. 16), it may be concluded that good chemical stability of tesamorelin can be obtained in the liquid formulation containing 10% HP-β-CD and mannitol as isotonicity agent. The formulation containing 10% HP-β-CD and 3% of mannitol as isotonicity agent, at pH 6.0±0.2 is found to be isotonic (303 mOsm/kg).

Chemical Stability.

The formulation comprising 8 mg/mL tesamorelin, 10% HP-β-CD, 3.5% of mannitol, and 10 mM of sodium lactate at pH 6 was stored at 15° C., 25° C., 37° C., and 45° C. for 12-21 days. The formulation containing 8 mg/mL in the presence of 5% mannitol was also stressed under the same conditions for comparison.

Figure 17:
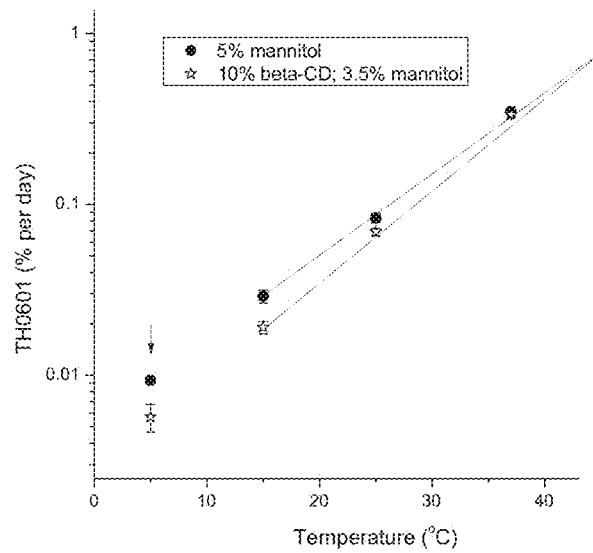
FIG. 17 shows the extrapolation of the rate of TH0601 formation in accelerated stability studies to the 5° C. conditions (shown by the arrow). The rate of TH0601 formation in control formulation (5% mannitol) is shown for comparison.
Figure 18:
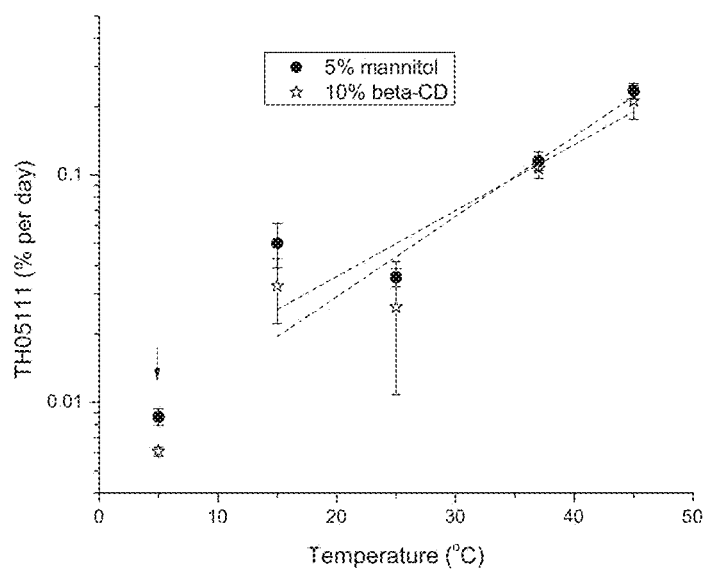
FIG. 18 shows the extrapolation of the rate of the TH05111 formation in accelerated stability studies to the 5° C. conditions (shown by the arrow). The rate of the TH05111 formation in control formulation (5% mannitol) is shown for comparison.

The samples were analyzed for purity of tesamorelin and relative abundance of deamidation products (TH0601 and TH05111). The results were analyzed in terms of zero-order degradation reaction kinetics, and the rate constants obtained at different temperatures were extrapolated to the target 5° C. conditions (FIGS. 17-18).

On the basis of the accelerated stability results, the approximate level of the deamidation products (TH0601 and TH05111) of tesamorelin at 5° C. can be estimated for long term storage of the liquid formulation, as presented in Table 4.

TABLE 4

Level of deamidation products (TH0601 and TH05111) after 2 years of storage at 5° C., predicted from analysis of the degradation rates of tesamorelin at 15° C., 25° C., 37° C., and 45° C.

| Parameter | Control formulation (5% mannitol) | Formulation 8 mg/mL tesamorelin, 10% HP—B—CD, 3% mannitol, pH 6 | Improvement |
| --- | --- | --- | --- |
| TH0601 | 6.81 ± 0.14 | 4.15 ± 0.77 | 39% |
| TH05111 | 6.31 ± 0.53 | 4.44 ± 0.21 | 30% |

On the basis of the real-time stability results, the approximate rate of the deamidation products (TH0601 and TH05111) formation at 25° C. can be estimated for long term storage of the freeze-dried formulation, as presented in Table 5

TABLE 5

The level of deamidated products (TH0601 and TH05111) and approximate rate of their formation in freeze-dried formulation composed of 8 mg/mL tesamorelin, 10% HP-B-CD, 3% mannitol, pH 6, after storage at 25° C.

| Compound | Time, months | | | | | Rate, %/year* |
| --- | --- | --- | --- | --- | --- | --- |
| | 0 | 1 | 3 | 5 | 6 | |
| TH0601 | 0.07 | 0.06 | 0.25 | 0.13 | 0.21 | 0.24 |
| TH05111 | 0.62 | 0.69 | 0.90 | 0.69 | 0.80 | 0.25 |

*-calculated by assuming linear increase in the level of impurity with time

Besides improved physical stability, the results indicate a significant reduction in the level of deamidated species (TH0601 and TH0511) in the formulation containing 10% of HP-β-CD compared to control formulation.

Example 6

Effect of HP-β-CD on Deamidation/Isomerization of Asx Residue

In order to verify whether the stabilizing effect of HP-β-CD against deamidation/isomerization at position 8 is specific to Asn$^8$ and hence unique for GRF structure, degradation of the compound bearing Asp at position 8, i.e. TH05111, in the presence of HP-β-CD, was investigated and compared to that of tesamorelin. Isomerization of Asp$^8$ in the structure of TH05111 leads to formation of the tesamorelin degradant TH0601, which makes it possible to monitor degradation by using the same chromatographic conditions as for tesamorelin.

Figure 19:
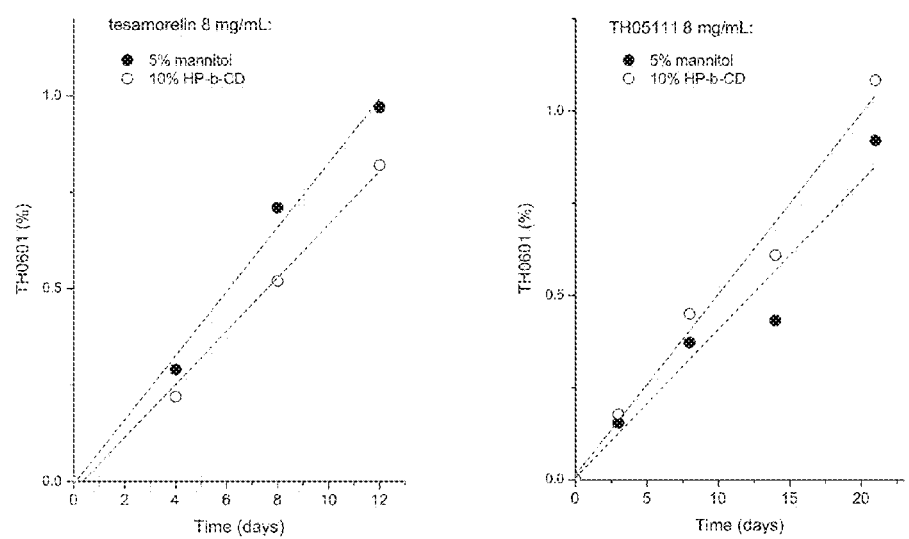
FIG. 19 shows the formation of isomerized $\beta$-$Asp^8$ product TH0601 upon incubation of tesamorelin (left panel) and TH05111 (right panel) in the solutions containing either 5% mannitol or 10% HP-$\beta$-CD at pH 6. The peptide concentrations are 8 mg/mL for both tesamorelin and TH05111.

The comparison of the kinetics of TH0601 formation in the solutions containing 8 mg/mL of TH05111 or tesamorelin with and without HP-β-CD is shown in FIG. 19.

It was found that isomerization of the $Asp^8$ residue in TH05111 is facilitated in the presence of HP-β-CD (FIG. 19). This is in contrast with apparent stabilizing action of HP-β-CD against deamidation/isomerization of $Asn^8$ residues in tesamorelin. On the basis of these experimental data, one can conclude that inhibition of deamidation/isomerization of the residue at position 8 by HP-β-CD is selective when the residue is Asn and hence somewhat unique for the GRF sequence.

Example 7

Effect of Methyl-β-Cyclodextrin on Deamidation and Isomerization of the $Asn^8$ Residue in Tesamorelin In addition to the studies described herein demonstrating the stabilizing effect of hydroxypropyl-b-cyclodextrin (HP-β-CD) against deamidation/isomerization of tesamorelin's $Asn^8$ residue, the effect of methyl-3-cyclodextrin (M-β-CD) was also tested, to verify that a similar stabilizing effect could be obtained with a different 3-cyclodextrin molecule.

Methyl-β-cyclodextrin (M-β-CD) produced by Wacker Life Science® was obtained from Sigma. The formulations containing 8 mg/ml of tesamorelin in the presence of 5% (w/v) of M-β-CD and 4.25% (w/v) mannitol for isotonicity were prepared at pH 4.5 and pH 6.0. The 8 mg/mL tesamorelin formulations containing 5% mannitol at pH 4.5 and pH 6.0 served as controls. All formulations contained 0.3% of m-cresol for antimicrobial protection. The formulations were stored at 25° C. for 1 month.

Figure 20:
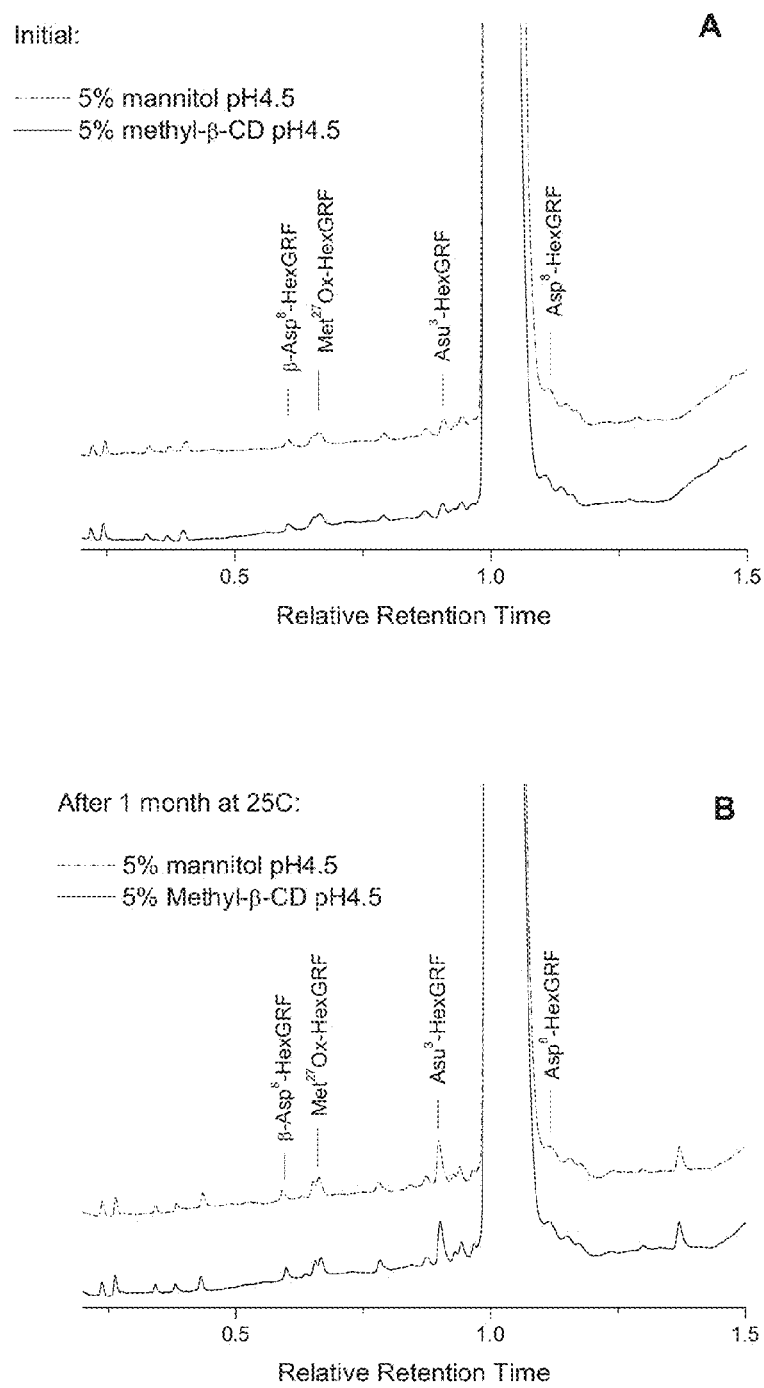
FIG. 20 shows the HPLC chromatograms of tesamorelin and its degradants in M-$\beta$-CD and M-$\beta$-CD-free formulations at pH 4.5 prior to (A) and after (B) incubation at 25° C. for 1 month.
Figure 21:
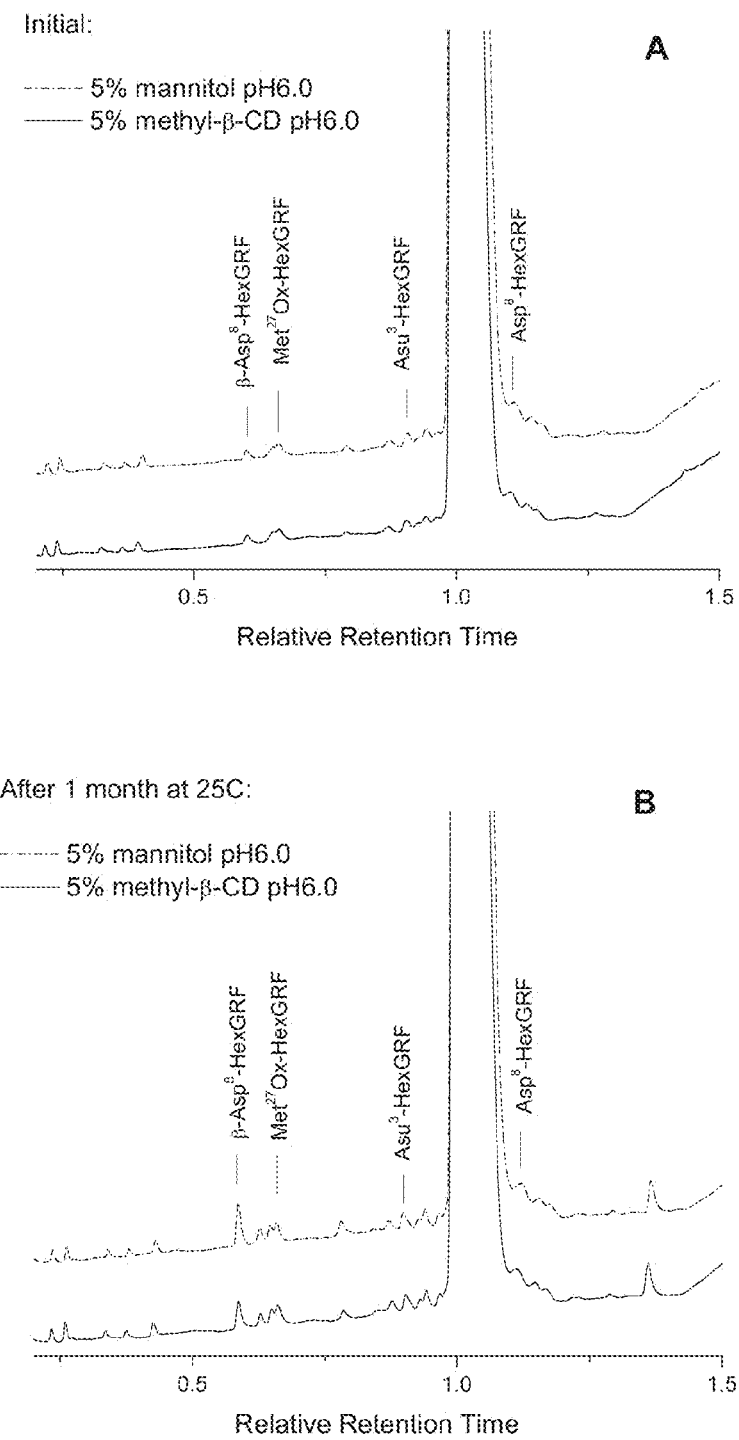
FIG. 21 shows the HPLC chromatograms of tesamorelin and its degradants in M-$\beta$-CD and M-$\beta$-CD-free formulations at pH 6.0 prior to (A) and after (B) incubation at 25° C. for 1 month.

After 1 month, the samples were analyzed by HPLC for tesamorelin purity and abundance of deamidation products. The chromatograms are shown in FIGS. 20 and 21. The results of chromatogram integrations are summarized in Table 6.

TABLE 6

Results of chromatogram integration after incubation of tested formulations for 1 month at 25° C.

| Formulation | β-$Asp^8$-HexGRF (TH0601) | | $Asp^8$-HexGRF (TH05111) | | $Asu^3$-HexGRF (TH1063) | |
| --- | --- | --- | --- | --- | --- | --- |
| | Initial | 1 month | Initial | 1 month | Initial | 1 month |
| 5% mannitol pH 4.5 | 0.10 | 0.11 | 0.67 | 0.72 | 0.16 | 0.42 |
| 5% M-β-CD pH 4.5 | 0.08 | 0.11 | 0.75 | 0.67 | 0.15 | 0.48 |
| 5% mannitol pH 6.0 | 0.08 | 0.32 | 0.78 | 0.82 | 0.17 | 0.19 |
| 5% M-β-CD pH 6.0 | 0.12 | 0.23 | 0.79 | 0.81 | 0.14 | 0.23 |

At pH 4.5, deamidation/isomerization in both formulations proceeds very slowly. The rate of $Asp^3$ cyclization to give $Asu^3$ is apparently not affected by either excipient.

At pH 6.0, the level of $Asu^3$-HexGRF remains unaffected by the presence of excipients. However, similar to the effect of HP-β-CD, deamidation/isomerization is substantially suppressed in the presence of M-β-CD, as seen from the level of β-$Asp^8$-HexGRF (Table 6 and FIG. 21B).

Sequences Described Herein:

```
                                       SEQ ID NO: 1
Xaa Xaa Asp Ala Ile Phe Thr Asn Ser Tyr Arg Lys
1               5                   10

Xaa Leu Xaa Gln Leu Xaa Ala Arg Lys Leu Leu Xaa
            15                  20

Xaa Ile Xaa Xaa Arg Xaa Xaa Xaa Xaa Xaa Xaa Xaa
25                  30                      35

Xaa Xaa Xaa Xaa Xaa Xaa Xaa Xaa
                40
``` wherein:

Xaa1=Tyr or His;

Xaa2=Val or Ala;

Xaa13=Val or Ile;

Xaa15=Ala or Gly;

Xaa18=Ser or Tyr;

Xaa24=Gln or His;

Xaa25=Asp or Glu;

Xaa27=Met or Ile or Nle;

Xaa28=Ser or Asn; and each of Xaa30 to Xaa44 is independently any amino acid or is absent.

```
                                       SEQ ID NO: 2
Tyr Ala Asp Ala Ile Phe Thr Asn Ser Tyr Arg Lys
1               5                   10

Val Leu Gly Gln Leu Ser Ala Arg Lys Leu Leu Gln
            15                  20

Asp Ile Met Ser Arg Gln Gln Gly Glu Ser Asn Gln
25                  30                      35

Glu Arg Gly Ala Arg Ala Arg Leu
                40
``` wherein Leu44 is capped with an unsubstituted amide moiety.

(Amino acid sequence of human GRF)

```
                                       SEQ ID NO: 3
Tyr Ala Asp Ala Ile Phe Thr Asn Ser Tyr Arg Lys
1               5                   10

Val Leu Gly Gln Leu Ser Ala Arg Lys Leu Leu Gln
            15                  20

Asp Ile Met Ser Arg Gln Gln Gly Glu Ser Asn Gln
25                  30                      35

Glu Arg Gly Ala Arg Ala Arg Leu
                40
```

```
                                       SEQ ID NO: 4
Tyr Ala Asp Ala Ile Phe Thr Asn Ser Tyr Arg Lys
1               5                   10

Val Leu Gly Gln Leu Ser Ala Arg Lys Leu Leu Gln
            15                  20

Asp Ile Met Ser Arg
25
``` wherein Arg29 is capped with an unsubstituted amide moiety.

(Amino acid sequence of minimum active core of human GRF)

SEQ ID NO: 5

Tyr Ala Asp Ala Ile Phe Thr Asn Ser Tyr Arg Lys
1               5                       10

Val Leu Gly Gln Leu Ser Ala Arg Lys Leu Leu Gln
            15                  20

Asp Ile Met Ser Arg
25

(Amino acid sequence corresponding to positions 30 to 44 of human GRF)

SEQ ID NO: 6

Gln Gln Gly Glu Ser Asn Gln Glu Arg Gly Ala Arg
1               5                       10

Ala Arg Leu
        15

SEQ ID NO: 7

Tyr Ala Asp Ala Ile Phe Thr Asn Ser Tyr Arg Lys
1               5                       10

Val Leu Gly Gln Leu Ser Ala Arg Lys Leu Leu Gln
            15                  20

Asp Ile Met Ser Arg Gln Gln Gly Glu Ser Asn Gln
25                  30                  35

Glu Arg Gly Ala Arg Ala Arg Leu
                40 wherein:

Tyr1 is linked to a trans-3-hexenoyl moiety; and

Leu44 is capped with an unsubstituted amide moiety.

Although the present invention has been described hereinabove by way of specific embodiments thereof, it can be modified, without departing from the spirit and nature of the subject invention as defined in the appended claims.

---

What is claimed is:

1. A liquid pharmaceutical formulation comprising:
   [trans-3-hexenoyl]hGRF(1-44) amide (SEQ ID NO: 7) or a pharmaceutically acceptable salt thereof, in an amount of about 1 mg/ml to about 10 mg/ml; and
   a modified β-cyclodextrin at a concentration of about 5% to about 10% (w/v),
wherein said formulation is isotonic and has a pH of about 5.5 to about 6.5, and wherein said modified β-cyclodextrin is not conjugated to said [trans-3-hexenoyl]hGRF(1-44) amide or pharmaceutically acceptable salt thereof.

2. The formulation of claim 1, wherein the formulation has a tonicity of about 250 to about 350 mOsm/L.

3. The formulation of claim 1, wherein the modified β-cyclodextrin is hydroxypropyl-β-cyclodextrin (HP-β-CD).

4. The formulation of claim 1, wherein the modified β-cyclodextrin is methyl-β-cyclodextrin (M-β-CD).

5. The formulation of claim 1, having a pH of about 5.8 to about 6.2.

6. The formulation of claim 1, further comprising an anti-microbial agent.

7. The formulation of claim 6, wherein the anti-microbial agent is m-cresol, benzyl alcohol, benzalkonium chloride, phenol or a combination thereof.

8. The formulation of claim 1, wherein the [trans-3-hexenoyl]hGRF(1-44) amide or pharmaceutically acceptable salt thereof is present in an amount of about 4 to about 8 mg/ml.

9. The formulation of claim 8, wherein the [trans-3-hexenoyl]hGRF(1-44) amide or pharmaceutically acceptable salt thereof is present in an amount of about 8 mg/ml.

10. The formulation of claim 1, comprising:
    about 4 to about 8 mg/mL of [trans-3-hexenoyl]hGRF(1-44) amide or a pharmaceutically acceptable salt thereof,
    about 5 to about 10% (w/v) of a modified β-cyclodextrin, wherein the modified β-cyclodextrin is hydroxypropyl-β-cyclodextrin, methyl-β-cyclodextrin, or a combination thereof,
said formulation having a pH of about 5.5 to about 6.0.

11. The formulation of claim 10, wherein the formulation has a tonicity of about 250 to about 350 mOsm/L.

12. The formulation of claim 10, wherein at least 70% of the [trans-3-hexenoyl]hGHRH (1-44) amide or pharmaceutically acceptable salt thereof is not deamidated at $Asn^8$ after 2 years of storage at temperature conditions of about 2° C. to about 8° C.

13. The formulation of claim 12, wherein at least 90% of the [trans-3-hexenoyl]hGHRH (1-44) amide or pharmaceutically acceptable salt thereof is not deamidated at $Asn^8$ after 2 years of storage at temperature conditions of about 2° C. to about 8° C.

14. A lyophilized or dehydrated pharmaceutical formulation prepared by lyophilizing or dehydrating the pharmaceutical formulation of claim 2.

15. The lyophilized or dehydrated formulation of claim 14, wherein at least 70% of the [trans-3-hexenoyl]hGRF (1-44) amide or pharmaceutically acceptable salt thereof is not deamidated at $Asn^8$ after 3 years of storage at temperature conditions of about 15° C. to about 25° C.

16. The lyophilized or dehydrated formulation of claim 15, wherein at least 90% of the [trans-3-hexenoyl]hGRF (1-44) amide or pharmaceutically acceptable salt thereof is not deamidated at $Asn^8$ after 3 years of storage at temperature conditions of about 15° C. to about 25° C.

17. A method of stabilizing [trans-3-hexenoyl]hGRF (1-44) amide or a pharmaceutically acceptable salt thereof in a liquid pharmaceutical formulation, the method comprising combining the [trans-3-hexenoyl]hGRF (1-44) amide or pharmaceutically acceptable salt thereof in an amount of about 1 to about 10 mg/mL with a modified β-cyclodextrin at a concentration of about 5% to about 10% (w/v), wherein the modified β-cyclodextrin is not conjugated to the [trans-3-hexenoyl]hGRF (1-44) amide or pharmaceutically acceptable salt thereof, and wherein the formulation is isotonic and has a pH of about 5.5 to about 6.5.

18. The method of claim 17, comprising:
    (a) combining the [trans-3-hexenoyl]hGRF (1-44) amide or pharmaceutically acceptable salt thereof with the modified β-cyclodextrin in an aqueous solution, wherein the modified β-cyclodextrin is not conjugated to the [trans-3-hexenoyl]hGRF (1-44) amide or pharmaceutically acceptable salt thereof;

(b) adjusting the pH of the solution to about 5.5 to about 6.5; and (c) lyophilizing or dehydrating the solution.

19. A method of inhibiting $Asn^8$ deamidation of [trans-3-hexenoyl]hGRF (1-44) amide or a pharmaceutically acceptable salt thereof in a liquid pharmaceutical formulation, the method comprising combining the [trans-3-hexenoyl]hGRF (1-44) amide or pharmaceutically acceptable salt thereof in an amount of about 1 to about 10 mg/mL with a modified β-cyclodextrin at a concentration of about 5% to about 10% (w/v), wherein the modified β-cyclodextrin is not conjugated to the GRF molecule or pharmaceutically acceptable salt thereof, and wherein the formulation is isotonic and has a pH of about 5.5 to about 6.5.

20. The method of claim 19, comprising:
   (a) combining the [trans-3-hexenoyl]hGRF (1-44) amide or pharmaceutically acceptable salt thereof with the modified β-cyclodextrin in an aqueous solution, wherein the modified β-cyclodextrin is not conjugated to the [trans-3-hexenoyl]hGRF (1-44) amide or pharmaceutically acceptable salt thereof; and
   (b) adjusting the pH of the solution to about 5.5 to about 6.5.

21. The method of claim 20, further comprising lyophilizing or dehydrating the solution after step (b).

22. The method of claim 19, wherein the modified β-cyclodextrin is hydroxypropyl-β-cyclodextrin (HP-β-CD), methyl-β-cyclodextrin (M-β-CD), or a combination thereof.

23. A suspension obtained by reconstituting the lyophilized or dehydrated pharmaceutical formulation of claim 14 with a suitable aqueous solution.

* * * * *